United States Patent
Tearney et al.

(10) Patent No.: US 9,968,245 B2
(45) Date of Patent: May 15, 2018

(54) APPARATUS AND METHOD FOR OBTAINING AND PROVIDING IMAGING INFORMATION ASSOCIATED WITH AT LEAST ONE PORTION OF A SAMPLE, AND EFFECTING SUCH PORTION(S)

(75) Inventors: Guillermo J. Tearney, Cambridge, MA (US); Brett Eugene Bouma, Quincy, MA (US); Dvir Yelin, Haifa (IL)

(73) Assignee: The General Hospital Corporation, Boston, MA (US)

( * ) Notice: Subject to any disclaimer, the term of this patent is extended or adjusted under 35 U.S.C. 154(b) by 124 days.

(21) Appl. No.: 13/614,459

(22) Filed: Sep. 13, 2012

(65) Prior Publication Data
US 2013/0066215 A1   Mar. 14, 2013

Related U.S. Application Data

(62) Division of application No. 11/875,676, filed on Oct. 19, 2007, now Pat. No. 8,838,213.
(Continued)

(51) Int. Cl.
*A61B 1/07*   (2006.01)
*A61B 5/00*   (2006.01)
(Continued)

(52) U.S. Cl.
CPC .............. *A61B 1/07* (2013.01); *A61B 5/0066* (2013.01); *A61B 5/0075* (2013.01);
(Continued)

(58) Field of Classification Search
CPC .............. A61B 5/0066; G01B 2290/30; G01B 2290/20; G01B 9/0205; G01B 9/02036; G01B 9/02028; G01B 9/02019
(Continued)

(56) References Cited

U.S. PATENT DOCUMENTS 2,339,754 A   1/1944  Brace
3,090,753 A   5/1963  Matuszak et al.
(Continued)

FOREIGN PATENT DOCUMENTS

CN   1550203   12/2004
DE   102005034443   2/2007
(Continued)

OTHER PUBLICATIONS

Notice of Allowance and Fees dated Nov. 23, 2010 for U.S. Appl. No. 12/627,918.
(Continued)

*Primary Examiner* — Hwa Lee
(74) *Attorney, Agent, or Firm* — Quarles & Brady LLP

(57) ABSTRACT

Exemplary apparatus and process can be provided for imaging information associated with at least one portion of a sample. For example, (i) first different wavelengths of at least one first electro-magnetic radiation can be provided within a first wavelength range provided on the portion of the sample so as to determine at least one first transverse location of the portion, and (ii) second different wavelengths of at least one second electro-magnetic radiation within a second wavelength range can be provided on the portion so as to determine at least one second transverse location of the portion. The first and second ranges can east partially overlap on the portion. Further, a relative phase between at least one third electro-magnetic radiation electro-magnetic radiation being returned from the sample and at least one fourth electro-magnetic radiation returned from a reference can be obtained to determine a relative depth location of the portion.

13 Claims, 11 Drawing Sheets

Related U.S. Application Data

(60) Provisional application No. 60/862,205, filed on Oct. 19, 2006.

(51) Int. Cl.
  *A61B 18/22* (2006.01)
  *A61B 17/00* (2006.01)

(52) U.S. Cl.
  CPC .......... *A61B 5/0084* (2013.01); *A61B 5/0086* (2013.01); *A61B 18/22* (2013.01); *A61B 2017/00061* (2013.01)

(58) Field of Classification Search
  USPC .................................................. 356/479, 497
  See application file for complete search history.

(56) References Cited

U.S. PATENT DOCUMENTS

| | | |
|---|---|---|
| 3,601,480 A | 8/1971 | Randall |
| 3,856,000 A | 12/1974 | Chikama |
| 3,872,407 A | 3/1975 | Hughes |
| 3,941,121 A | 3/1976 | Olinger |
| 3,973,219 A | 8/1976 | Tang et al. |
| 3,983,507 A | 9/1976 | Tang et al. |
| 4,030,827 A | 6/1977 | Delhaye et al. |
| 4,030,831 A | 6/1977 | Gowrinathan |
| 4,140,364 A | 2/1979 | Yamashita et al. |
| 4,141,362 A | 2/1979 | Wurster |
| 4,224,929 A | 9/1980 | Furihata |
| 4,295,738 A | 10/1981 | Meltz et al. |
| 4,300,816 A | 11/1981 | Snitzer et al. |
| 4,303,300 A | 12/1981 | Pressiat et al. |
| 4,428,643 A | 1/1984 | Kay |
| 4,479,499 A | 10/1984 | Alfano et al. |
| 4,533,247 A | 8/1985 | Epworth |
| 4,585,349 A | 4/1986 | Gross et al. |
| 4,601,036 A | 7/1986 | Faxvog et al. |
| 4,607,622 A | 8/1986 | Fritch et al. |
| 4,631,498 A | 12/1986 | Cutler |
| 4,639,999 A | 2/1987 | Daniele |
| 4,650,327 A | 3/1987 | Ogi |
| 4,734,578 A | 3/1988 | Horikawa |
| 4,744,656 A | 5/1988 | Moran et al. |
| 4,751,706 A | 6/1988 | Rohde et al. |
| 4,763,977 A | 8/1988 | Kawasaki et al. |
| 4,770,492 A | 9/1988 | Levin et al. |
| 4,827,907 A | 5/1989 | Tashiro |
| 4,834,111 A | 5/1989 | Khanna et al. |
| 4,868,834 A | 9/1989 | Fox et al. |
| 4,890,901 A | 1/1990 | Cross, Jr. |
| 4,892,406 A | 1/1990 | Waters |
| 4,905,169 A | 2/1990 | Buican et al. |
| 4,909,631 A | 3/1990 | Tan et al. |
| 4,925,302 A | 5/1990 | Cutler |
| 4,928,005 A | 5/1990 | Lefèvre et al. |
| 4,940,328 A | 7/1990 | Hartman |
| 4,965,441 A | 10/1990 | Picard |
| 4,965,599 A | 10/1990 | Roddy et al. |
| 4,966,589 A | 10/1990 | Kaufman |
| 4,984,888 A | 1/1991 | Tobias et al. |
| 4,993,834 A | 2/1991 | Carlhoff et al. |
| 4,998,972 A | 3/1991 | Chin et al. |
| 5,039,193 A | 8/1991 | Snow et al. |
| 5,040,889 A | 8/1991 | Keane |
| 5,045,936 A | 9/1991 | Lobb et al. |
| 5,046,501 A | 9/1991 | Crilly |
| 5,065,331 A | 11/1991 | Vachon et al. |
| 5,085,496 A | 2/1992 | Yoshida et al. |
| 5,120,953 A | 6/1992 | Harris |
| 5,121,983 A | 6/1992 | Lee |
| 5,127,730 A | 7/1992 | Brelje et al. |
| 5,177,488 A | 1/1993 | Wang et al. |
| 5,197,470 A | 3/1993 | Helfer et al. |
| 5,202,745 A | 4/1993 | Sorin et al. |
| 5,202,931 A | 4/1993 | Bacus et al. |
| 5,208,651 A | 5/1993 | Buican |
| 5,212,667 A | 5/1993 | Tomlinson et al. |
| 5,214,538 A | 5/1993 | Lobb |
| 5,217,456 A | 6/1993 | Narciso, Jr. |
| 5,228,001 A | 7/1993 | Birge et al. |
| 5,241,364 A | 8/1993 | Kimura |
| 5,248,876 A | 9/1993 | Kerstens et al. |
| 5,250,186 A | 10/1993 | Dollinger et al. |
| 5,251,009 A | 10/1993 | Bruno |
| 5,262,644 A | 11/1993 | Maguire |
| 5,275,594 A | 1/1994 | Baker |
| 5,281,811 A | 1/1994 | Lewis |
| 5,283,795 A | 2/1994 | Fink |
| 5,291,885 A | 3/1994 | Taniji et al. |
| 5,293,872 A | 3/1994 | Alfano et al. |
| 5,293,873 A | 3/1994 | Fang |
| 5,302,025 A | 4/1994 | Kleinerman |
| 5,304,173 A | 4/1994 | Kittrell et al. |
| 5,304,810 A | 4/1994 | Amos |
| 5,305,759 A | 4/1994 | Kaneko et al. |
| 5,317,389 A | 5/1994 | Hochberg et al. |
| 5,318,024 A | 6/1994 | Kittrell et al. |
| 5,321,501 A | 6/1994 | Swanson et al. |
| 5,333,144 A | 7/1994 | Liedenbaum et al. |
| 5,348,003 A | 9/1994 | Caro |
| 5,353,790 A | 10/1994 | Jacques et al. |
| 5,383,467 A | 1/1995 | Auer et al. |
| 5,394,235 A | 2/1995 | Takeuchi et al. |
| 5,400,771 A | 3/1995 | Pirak et al. |
| 5,404,415 A | 4/1995 | Mori et al. |
| 5,411,016 A | 5/1995 | Kume et al. |
| 5,414,509 A | 5/1995 | Veligdan |
| 5,419,323 A | 5/1995 | Kittrell et al. |
| 5,424,827 A | 6/1995 | Horwitz et al. |
| 5,439,000 A | 8/1995 | Gunderson et al. |
| 5,441,053 A | 8/1995 | Lodder et al. |
| 5,450,203 A | 9/1995 | Penkethman |
| 5,454,807 A | 10/1995 | Lennox et al. |
| 5,459,325 A | 10/1995 | Hueton et al. |
| 5,459,570 A | 10/1995 | Swanson et al. |
| 5,465,147 A | 11/1995 | Swanson |
| 5,479,928 A | 1/1996 | Cathignoal et al. |
| 5,486,701 A | 1/1996 | Norton et al. |
| 5,491,524 A | 2/1996 | Hellmuth et al. |
| 5,491,552 A | 2/1996 | Kittrell |
| 5,522,004 A | 5/1996 | Djupsjobacka et al. |
| 5,526,338 A | 6/1996 | Hasman et al. |
| 5,555,087 A | 9/1996 | Miyagawa et al. |
| 5,562,100 A | 10/1996 | Kittrell et al. |
| 5,565,983 A | 10/1996 | Barnard et al. |
| 5,565,986 A | 10/1996 | Knüttel |
| 5,566,267 A | 10/1996 | Neuberger |
| 5,583,342 A | 12/1996 | Ichie |
| 5,590,660 A | 1/1997 | MacAulay et al. |
| 5,600,486 A | 2/1997 | Gal et al. |
| 5,601,087 A | 2/1997 | Richards-Kortum et al. |
| 5,621,830 A | 4/1997 | Lucey et al. |
| 5,623,336 A | 4/1997 | Raab |
| 5,628,313 A | 5/1997 | Webster, Jr. |
| 5,635,830 A | 6/1997 | Itoh |
| 5,649,924 A | 7/1997 | Everett et al. |
| 5,697,373 A | 12/1997 | Gunderson et al. |
| 5,698,397 A | 12/1997 | Zarling et al. |
| 5,701,155 A | 12/1997 | Welch et al. |
| 5,710,630 A | 1/1998 | Essenpreis et al. |
| 5,716,324 A | 2/1998 | Toida |
| 5,719,399 A | 2/1998 | Alfano et al. |
| 5,730,731 A | 3/1998 | Mollenauer et al. |
| 5,735,276 A | 4/1998 | Lemelson |
| 5,740,808 A | 4/1998 | Panescu et al. |
| 5,748,318 A | 5/1998 | Maris et al. |
| 5,748,598 A | 5/1998 | Swanson et al. |
| 5,752,518 A | 5/1998 | McGee et al. |
| 5,784,352 A | 7/1998 | Swanson et al. |
| 5,785,651 A | 7/1998 | Kuhn et al. |
| 5,795,295 A | 8/1998 | Hellmuth et al. |
| 5,801,826 A | 9/1998 | Williams |
| 5,801,831 A | 9/1998 | Sargoytchev et al. |

(56) References Cited

U.S. PATENT DOCUMENTS

| | | |
|---|---|---|
| 5,803,082 A | 9/1998 | Stapleton et al. |
| 5,807,261 A | 9/1998 | Benaron et al. |
| 5,810,719 A | 9/1998 | Toida |
| 5,817,144 A | 10/1998 | Gregory |
| 5,829,439 A | 11/1998 | Yokosawa et al. |
| 5,836,877 A | 11/1998 | Zavislan et al. |
| 5,840,023 A | 11/1998 | Oraevsky et al. |
| 5,840,031 A | 11/1998 | Crowley |
| 5,840,075 A | 11/1998 | Mueller et al. |
| 5,842,995 A | 12/1998 | Mahadevan-Jansen et al. |
| 5,843,000 A | 12/1998 | Nishioka et al. |
| 5,843,052 A | 12/1998 | Benja-Athon |
| 5,847,827 A | 12/1998 | Fercher |
| 5,862,273 A | 1/1999 | Pelletier |
| 5,865,754 A | 2/1999 | Sevick-Muraca et al. |
| 5,867,268 A | 2/1999 | Gelikonov et al. |
| 5,871,449 A | 2/1999 | Brown |
| 5,872,879 A | 2/1999 | Hamm |
| 5,877,856 A | 3/1999 | Fercher |
| 5,887,009 A | 3/1999 | Mandella et al. |
| 5,892,583 A | 4/1999 | Li |
| 5,910,839 A | 6/1999 | Erskine |
| 5,912,764 A | 6/1999 | Togino |
| 5,920,373 A | 7/1999 | Bille |
| 5,920,390 A | 7/1999 | Farahi et al. |
| 5,921,926 A | 7/1999 | Rolland et al. |
| 5,926,592 A | 7/1999 | De Boer et al. |
| 5,949,929 A | 9/1999 | Hamm |
| 5,951,482 A | 9/1999 | Winston et al. |
| 5,955,737 A | 9/1999 | Hallidy et al. |
| 5,956,355 A | 9/1999 | Swanson et al. |
| 5,968,064 A | 10/1999 | Selmon et al. |
| 5,975,697 A | 11/1999 | Hellmuth et al. |
| 5,983,125 A | 11/1999 | Alfano et al. |
| 5,987,346 A | 11/1999 | Benaron et al. |
| 5,991,697 A | 11/1999 | Nelson et al. |
| 5,994,690 A | 11/1999 | Kulkarni et al. |
| 5,995,223 A | 11/1999 | Power |
| 6,002,480 A | 12/1999 | Izatt et al. |
| 6,004,314 A | 12/1999 | Wei et al. |
| 6,006,128 A | 12/1999 | Izatt et al. |
| 6,007,996 A | 12/1999 | McNamara et al. |
| 6,010,449 A | 1/2000 | Selmon et al. |
| 6,014,214 A | 1/2000 | Li |
| 6,016,197 A | 1/2000 | Krivoshlykov |
| 6,020,963 A | 2/2000 | Dimarzio et al. |
| 6,025,956 A | 2/2000 | Nagano et al. |
| 6,033,721 A | 3/2000 | Nassuphis |
| 6,037,579 A | 3/2000 | Chan et al. |
| 6,044,288 A | 3/2000 | Wake et al. |
| 6,045,511 A | 4/2000 | Lutz et al. |
| 6,048,742 A | 4/2000 | Weyburne et al. |
| 6,052,186 A | 4/2000 | Tsai |
| 6,053,613 A | 4/2000 | Wei et al. |
| 6,069,698 A | 5/2000 | Ozawa et al. |
| 6,078,047 A | 6/2000 | Mittleman et al. |
| 6,091,496 A | 7/2000 | Hill |
| 6,091,984 A | 7/2000 | Perelman et al. |
| 6,094,274 A | 7/2000 | Yokoi |
| 6,107,048 A | 8/2000 | Goldenring et al. |
| 6,111,645 A | 8/2000 | Tearney et al. |
| 6,117,128 A | 9/2000 | Gregory |
| 6,120,516 A | 9/2000 | Selmon et al. |
| 6,134,003 A | 10/2000 | Tearney et al. |
| 6,134,010 A | 10/2000 | Zavislan |
| 6,134,033 A | 10/2000 | Bergano et al. |
| 6,141,577 A | 10/2000 | Rolland et al. |
| 6,151,522 A | 11/2000 | Alfano et al. |
| 6,159,445 A | 12/2000 | Klaveness et al. |
| 6,160,826 A | 12/2000 | Swanson et al. |
| 6,161,031 A | 12/2000 | Hochman et al. |
| 6,166,373 A | 12/2000 | Mao |
| 6,174,291 B1 | 1/2001 | McMahon et al. |
| 6,175,669 B1 | 1/2001 | Colston et al. |
| 6,185,271 B1 | 2/2001 | Kinsinger |
| 6,191,862 B1 | 2/2001 | Swanson et al. |
| 6,193,676 B1 | 2/2001 | Winston et al. |
| 6,198,956 B1 | 3/2001 | Dunne |
| 6,201,989 B1 | 3/2001 | Whitehead et al. |
| 6,208,415 B1 | 3/2001 | De Boer et al. |
| 6,208,887 B1 | 3/2001 | Clarke |
| 6,245,026 B1 | 6/2001 | Campbell et al. |
| 6,249,349 B1 | 6/2001 | Lauer |
| 6,249,381 B1 | 6/2001 | Suganuma |
| 6,249,630 B1 | 6/2001 | Stock et al. |
| 6,263,234 B1 | 7/2001 | Engelhardt et al. |
| 6,264,610 B1 | 7/2001 | Zhu |
| 6,272,268 B1 | 8/2001 | Miller et al. |
| 6,272,376 B1 | 8/2001 | Marcu et al. |
| 6,274,871 B1 | 8/2001 | Dukor et al. |
| 6,282,011 B1 | 8/2001 | Tearney et al. |
| 6,297,018 B1 | 10/2001 | French et al. |
| 6,301,048 B1 | 10/2001 | Cao et al. |
| 6,308,092 B1 | 10/2001 | Hoyns |
| 6,324,419 B1 | 11/2001 | Guzelsu et al. |
| 6,341,036 B1 | 1/2002 | Tearney et al. |
| 6,353,693 B1 | 3/2002 | Kano et al. |
| 6,359,692 B1 | 3/2002 | Groot |
| 6,374,128 B1 | 4/2002 | Toida et al. |
| 6,377,349 B1 | 4/2002 | Fercher |
| 6,384,915 B1 | 5/2002 | Everett et al. |
| 6,393,312 B1 | 5/2002 | Hoyns |
| 6,394,964 B1 | 5/2002 | Sievert, Jr. et al. |
| 6,396,941 B1 | 5/2002 | Bacus et al. |
| 6,421,164 B2 | 7/2002 | Tearney et al. |
| 6,437,867 B2 | 8/2002 | Zeylikovich et al. |
| 6,441,892 B2 | 8/2002 | Xiao et al. |
| 6,441,959 B1 | 8/2002 | Yang et al. |
| 6,445,485 B1 | 9/2002 | Frigo et al. |
| 6,445,939 B1 | 9/2002 | Swanson et al. |
| 6,445,944 B1 | 9/2002 | Ostrovsky |
| 6,459,487 B1 | 10/2002 | Chen et al. |
| 6,463,313 B1 | 10/2002 | Winston et al. |
| 6,469,846 B2 | 10/2002 | Ebizuka et al. |
| 6,475,159 B1 | 11/2002 | Casscells et al. |
| 6,475,210 B1 | 11/2002 | Phelps et al. |
| 6,477,403 B1 | 11/2002 | Eguchi et al. |
| 6,485,413 B1 | 11/2002 | Boppart et al. |
| 6,485,482 B1 | 11/2002 | Belef |
| 6,501,551 B1 | 12/2002 | Tearney et al. |
| 6,501,878 B2 | 12/2002 | Hughes et al. |
| 6,516,014 B1 | 2/2003 | Sellin et al. |
| 6,517,532 B1 | 2/2003 | Altshuler et al. |
| 6,538,817 B1 | 3/2003 | Farmer et al. |
| 6,540,391 B2 | 4/2003 | Lanzetta et al. |
| 6,549,801 B1 | 4/2003 | Chen et al. |
| 6,552,796 B2 | 4/2003 | Magnin et al. |
| 6,556,305 B1 | 4/2003 | Aziz et al. |
| 6,556,853 B1 | 4/2003 | Cabib et al. |
| 6,558,324 B1 | 5/2003 | Von Behren et al. |
| 6,560,259 B1 | 5/2003 | Hwang et al. |
| 6,564,087 B1 | 5/2003 | Pitris et al. |
| 6,564,089 B2 | 5/2003 | Izatt et al. |
| 6,567,585 B2 | 5/2003 | De Boer et al. |
| 6,593,101 B2 | 7/2003 | Richards-Kortum et al. |
| 6,611,833 B1 | 8/2003 | Johnson et al. |
| 6,615,071 B1 | 9/2003 | Casscells, III et al. |
| 6,622,732 B2 | 9/2003 | Constantz |
| 6,654,127 B2 | 11/2003 | Everett et al. |
| 6,657,730 B2 | 12/2003 | Pfau et al. |
| 6,658,278 B2 | 12/2003 | Gruhl |
| 6,680,780 B1 | 1/2004 | Fee |
| 6,685,885 B2 | 2/2004 | Nolte et al. |
| 6,687,007 B1 | 2/2004 | Meigs |
| 6,687,010 B1 | 2/2004 | Horii et al. |
| 6,687,036 B2 | 2/2004 | Riza |
| 6,692,430 B2 | 2/2004 | Adler |
| 6,701,181 B2 | 3/2004 | Tang et al. |
| 6,721,094 B1 | 4/2004 | Sinclair et al. |
| 6,725,073 B1 | 4/2004 | Motamedi et al. |
| 6,738,144 B1 | 5/2004 | Dogariu et al. |
| 6,741,355 B2 | 5/2004 | Drabarek |
| 6,741,884 B1 | 5/2004 | Freeman et al. |
| 6,757,467 B1 | 6/2004 | Rogers |

(56) References Cited

U.S. PATENT DOCUMENTS

| | | |
|---|---|---|
| 6,790,175 B1 | 9/2004 | Furusawa et al. |
| 6,806,963 B1 | 10/2004 | Wälti et al. |
| 6,816,743 B2 | 11/2004 | Moreno et al. |
| 6,831,781 B2 | 12/2004 | Tearney et al. |
| 6,839,496 B1 | 1/2005 | Mills et al. |
| 6,882,432 B2 | 4/2005 | Deck |
| 6,900,899 B2 | 5/2005 | Nevis |
| 6,903,820 B2 | 6/2005 | Wang |
| 6,909,105 B1 | 6/2005 | Heintzmann et al. |
| 6,949,072 B2 | 9/2005 | Furnish et al. |
| 6,961,123 B1 | 11/2005 | Wang et al. |
| 6,980,299 B1 | 12/2005 | de Boer |
| 6,996,549 B2 | 2/2006 | Zhang et al. |
| 7,006,231 B2 | 2/2006 | Ostrovsky et al. |
| 7,006,232 B2 | 2/2006 | Rollins et al. |
| 7,019,838 B2 | 3/2006 | Izatt et al. |
| 7,027,633 B2 | 4/2006 | Foran et al. |
| 7,061,622 B2 | 6/2006 | Rollins et al. |
| 7,072,047 B2 | 7/2006 | Westphal et al. |
| 7,075,658 B2 | 7/2006 | Izatt et al. |
| 7,099,358 B1 | 8/2006 | Chong et al. |
| 7,113,288 B2 | 9/2006 | Fercher |
| 7,113,625 B2 | 9/2006 | Watson et al. |
| 7,130,320 B2 | 10/2006 | Tobiason et al. |
| 7,133,138 B2 * | 11/2006 | Horii et al. .......... 356/497 |
| 7,139,598 B2 | 11/2006 | Hull et al. |
| 7,142,835 B2 | 11/2006 | Paulus |
| 7,148,970 B2 | 12/2006 | De Boer |
| 7,177,027 B2 | 2/2007 | Hirasawa et al. |
| 7,190,464 B2 | 3/2007 | Alphonse |
| 7,230,708 B2 | 6/2007 | Lapotko et al. |
| 7,231,243 B2 | 6/2007 | Tearney et al. |
| 7,236,637 B2 | 6/2007 | Sirohey et al. |
| 7,242,480 B2 | 7/2007 | Alphonse |
| 7,267,494 B2 | 9/2007 | Deng et al. |
| 7,272,252 B2 | 9/2007 | De La Torre-Bueno et al. |
| 7,304,798 B2 | 12/2007 | Izumi et al. |
| 7,310,150 B2 | 12/2007 | Guillermo et al. |
| 7,330,270 B2 | 2/2008 | O'Hara et al. |
| 7,336,366 B2 | 2/2008 | Choma et al. |
| 7,342,659 B2 | 3/2008 | Horn et al. |
| 7,355,716 B2 | 4/2008 | De Boer et al. |
| 7,355,721 B2 | 4/2008 | Quadling et al. |
| 7,359,062 B2 | 4/2008 | Chen et al. |
| 7,365,858 B2 | 4/2008 | Fang-Yen et al. |
| 7,366,376 B2 | 4/2008 | Shishkov et al. |
| 7,382,809 B2 | 6/2008 | Chong et al. |
| 7,391,520 B2 | 6/2008 | Zhou et al. |
| 7,458,683 B2 | 12/2008 | Chernyak et al. |
| 7,530,948 B2 | 5/2009 | Seibel et al. |
| 7,539,530 B2 | 5/2009 | Caplan et al. |
| 7,609,391 B2 | 10/2009 | Betzig |
| 7,630,083 B2 | 12/2009 | de Boer et al. |
| 7,643,152 B2 | 1/2010 | de Boer et al. |
| 7,643,153 B2 | 1/2010 | de Boer et al. |
| 7,646,905 B2 | 1/2010 | Guittet et al. |
| 7,649,160 B2 | 1/2010 | Colomb et al. |
| 7,664,300 B2 | 2/2010 | Lange et al. |
| 7,733,497 B2 | 6/2010 | Yun et al. |
| 7,782,464 B2 | 8/2010 | Mujat et al. |
| 7,799,558 B1 | 9/2010 | Dultz |
| 7,805,034 B2 | 9/2010 | Kato et al. |
| 7,911,621 B2 | 3/2011 | Motaghiannezam et al. |
| 7,969,578 B2 | 6/2011 | Yun et al. |
| 7,973,936 B2 | 7/2011 | Dantus |
| 8,315,282 B2 | 11/2012 | Huber et al. |
| 2001/0020126 A1 | 9/2001 | Khoury |
| 2001/0036002 A1 | 11/2001 | Tearney et al. |
| 2001/0047137 A1 | 11/2001 | Moreno et al. |
| 2001/0055462 A1 | 12/2001 | Seibel |
| 2002/0016533 A1 | 2/2002 | Marchitto et al. |
| 2002/0024015 A1 | 2/2002 | Hoffmann et al. |
| 2002/0037252 A1 | 3/2002 | Toida et al. |
| 2002/0048025 A1 | 4/2002 | Takaoka |
| 2002/0048026 A1 | 4/2002 | Isshiki et al. |
| 2002/0052547 A1 | 5/2002 | Toida |
| 2002/0057431 A1 | 5/2002 | Fateley et al. |
| 2002/0064341 A1 | 5/2002 | Fauver et al. |
| 2002/0076152 A1 | 6/2002 | Hughes et al. |
| 2002/0085209 A1 | 7/2002 | Mittleman et al. |
| 2002/0086347 A1 | 7/2002 | Johnson et al. |
| 2002/0091322 A1 | 7/2002 | Chaiken et al. |
| 2002/0093662 A1 | 7/2002 | Chen et al. |
| 2002/0109851 A1 | 8/2002 | Deck |
| 2002/0113965 A1 | 8/2002 | Yun |
| 2002/0122182 A1 | 9/2002 | Everett et al. |
| 2002/0122246 A1 | 9/2002 | Tearney et al. |
| 2002/0140942 A1 | 10/2002 | Fee et al. |
| 2002/0158211 A1 | 10/2002 | Gillispie |
| 2002/0161357 A1 | 10/2002 | Rox et al. |
| 2002/0163622 A1 | 11/2002 | Magnin et al. |
| 2002/0166946 A1 | 11/2002 | Iizuka et al. |
| 2002/0168158 A1 | 11/2002 | Furusawa et al. |
| 2002/0172485 A1 | 11/2002 | Keaton et al. |
| 2002/0183623 A1 | 12/2002 | Tang et al. |
| 2002/0188204 A1 | 12/2002 | McNamara et al. |
| 2002/0196446 A1 | 12/2002 | Roth et al. |
| 2002/0198457 A1 | 12/2002 | Tearney et al. |
| 2003/0001071 A1 | 1/2003 | Mandella et al. |
| 2003/0013973 A1 | 1/2003 | Georgakoudi et al. |
| 2003/0023153 A1 | 1/2003 | Izatt et al. |
| 2003/0025917 A1 | 2/2003 | Suhami |
| 2003/0026735 A1 | 2/2003 | Nolte et al. |
| 2003/0028114 A1 | 2/2003 | Casscells, III et al. |
| 2003/0030816 A1 | 2/2003 | Eom et al. |
| 2003/0043381 A1 | 3/2003 | Fercher |
| 2003/0053673 A1 | 3/2003 | Dewaele |
| 2003/0067607 A1 | 4/2003 | Wolleschensky et al. |
| 2003/0082105 A1 | 5/2003 | Fischman et al. |
| 2003/0097048 A1 | 5/2003 | Ryan et al. |
| 2003/0103212 A1 | 6/2003 | Westphal et al. |
| 2003/0108911 A1 | 6/2003 | Klimant et al. |
| 2003/0120137 A1 | 6/2003 | Pawluczyk et al. |
| 2003/0135101 A1 | 7/2003 | Webler |
| 2003/0137669 A1 | 7/2003 | Rollins et al. |
| 2003/0164952 A1 | 9/2003 | Deichmann et al. |
| 2003/0165263 A1 | 9/2003 | Hamer et al. |
| 2003/0171691 A1 | 9/2003 | Casscells, III et al. |
| 2003/0174339 A1 | 9/2003 | Feldchtein et al. |
| 2003/0191392 A1 | 10/2003 | Haldeman |
| 2003/0199769 A1 | 10/2003 | Podoleanu et al. |
| 2003/0216719 A1 | 11/2003 | Debenedictis et al. |
| 2003/0218756 A1 | 11/2003 | Chen et al. |
| 2003/0220749 A1 | 11/2003 | Chen et al. |
| 2003/0236443 A1 | 12/2003 | Cespedes et al. |
| 2004/0002650 A1 | 1/2004 | Mandrusov et al. |
| 2004/0039252 A1 | 2/2004 | Koch |
| 2004/0039298 A1 | 2/2004 | Abreu |
| 2004/0054268 A1 | 3/2004 | Esenaliev et al. |
| 2004/0072200 A1 | 4/2004 | Rigler et al. |
| 2004/0075841 A1 | 4/2004 | Van Neste et al. |
| 2004/0076940 A1 | 4/2004 | Alexander et al. |
| 2004/0077949 A1 | 4/2004 | Blofgett et al. |
| 2004/0085540 A1 | 5/2004 | Lapotko et al. |
| 2004/0086245 A1 | 5/2004 | Farroni et al. |
| 2004/0095464 A1 | 5/2004 | Miyagi et al. |
| 2004/0100631 A1 | 5/2004 | Bashkansky et al. |
| 2004/0100681 A1 | 5/2004 | Bjarklev et al. |
| 2004/0110206 A1 | 6/2004 | Wong et al. |
| 2004/0126048 A1 | 7/2004 | Dave et al. |
| 2004/0126120 A1 | 7/2004 | Cohen et al. |
| 2004/0133191 A1 | 7/2004 | Momiuchi et al. |
| 2004/0150829 A1 | 8/2004 | Koch et al. |
| 2004/0150830 A1 | 8/2004 | Chan |
| 2004/0152989 A1 | 8/2004 | Puttappa et al. |
| 2004/0165184 A1 | 8/2004 | Mizuno |
| 2004/0166593 A1 | 8/2004 | Nolte et al. |
| 2004/0188148 A1 | 9/2004 | Chen et al. |
| 2004/0189999 A1 | 9/2004 | De Groot et al. |
| 2004/0204651 A1 | 10/2004 | Freeman et al. |
| 2004/0212808 A1 | 10/2004 | Okawa et al. |
| 2004/0239938 A1 | 12/2004 | Izatt et al. |
| 2004/0246490 A1 | 12/2004 | Wang |
| 2004/0246583 A1 | 12/2004 | Mueller et al. |

(56) References Cited

U.S. PATENT DOCUMENTS

| | | |
|---|---|---|
| 2004/0247268 A1 | 12/2004 | Ishihara et al. |
| 2004/0254474 A1 | 12/2004 | Seibel et al. |
| 2004/0258106 A1 | 12/2004 | Araujo et al. |
| 2004/0263843 A1 | 12/2004 | Knopp et al. |
| 2005/0004453 A1 | 1/2005 | Tearney et al. |
| 2005/0018133 A1 | 1/2005 | Huang et al. |
| 2005/0018200 A1 | 1/2005 | Guillermo et al. |
| 2005/0018201 A1 | 1/2005 | De Boer et al. |
| 2005/0035295 A1 | 2/2005 | Bouma et al. |
| 2005/0036150 A1 | 2/2005 | Izatt et al. |
| 2005/0046837 A1 | 3/2005 | Izumi et al. |
| 2005/0049488 A1 | 3/2005 | Homan |
| 2005/0057680 A1 | 3/2005 | Agan |
| 2005/0057756 A1 | 3/2005 | Fang-Yen et al. |
| 2005/0059894 A1 | 3/2005 | Zeng et al. |
| 2005/0065421 A1 | 3/2005 | Burckhardt et al. |
| 2005/0075547 A1 | 4/2005 | Wang |
| 2005/0083534 A1 | 4/2005 | Riza et al. |
| 2005/0119567 A1 | 6/2005 | Choi et al. |
| 2005/0128488 A1 | 6/2005 | Yelin et al. |
| 2005/0165303 A1 | 7/2005 | Kleen et al. |
| 2005/0171438 A1 | 8/2005 | Chen et al. |
| 2005/0190372 A1 | 9/2005 | Dogariu et al. |
| 2005/0197530 A1 | 9/2005 | Daniel et al. |
| 2005/0221270 A1 | 10/2005 | Connelly et al. |
| 2005/0254059 A1 | 11/2005 | Alphonse |
| 2005/0254061 A1 | 11/2005 | Alphonse et al. |
| 2006/0020172 A1 | 1/2006 | Luerssen et al. |
| 2006/0033923 A1 | 2/2006 | Hirasawa et al. |
| 2006/0039004 A1 | 2/2006 | De Boer et al. |
| 2006/0093276 A1 | 5/2006 | Bouma et al. |
| 2006/0100528 A1* | 5/2006 | Chan ............... A61B 3/102 600/476 |
| 2006/0103850 A1 | 5/2006 | Alphonse et al. |
| 2006/0106375 A1 | 5/2006 | Werneth et al. |
| 2006/0146339 A1 | 7/2006 | Fujita |
| 2006/0155193 A1 | 7/2006 | Leonardi et al. |
| 2006/0164639 A1 | 7/2006 | Horn et al. |
| 2006/0167363 A1 | 7/2006 | Bernstein et al. |
| 2006/0171503 A1 | 8/2006 | O'Hara et al. |
| 2006/0184048 A1 | 8/2006 | Saadat et al. |
| 2006/0189928 A1 | 8/2006 | Camus et al. |
| 2006/0193352 A1 | 8/2006 | Chong et al. |
| 2006/0224053 A1 | 10/2006 | Black et al. |
| 2006/0244973 A1 | 11/2006 | Yun et al. |
| 2006/0279742 A1 | 12/2006 | Tearney |
| 2007/0002435 A1 | 1/2007 | Ye et al. |
| 2007/0019208 A1 | 1/2007 | Toida et al. |
| 2007/0024860 A1 | 2/2007 | Tobiason et al. |
| 2007/0035743 A1 | 2/2007 | Vakoc et al. |
| 2007/0038040 A1 | 2/2007 | Cense et al. |
| 2007/0048818 A1 | 3/2007 | Rosen et al. |
| 2007/0070496 A1 | 3/2007 | Gweon et al. |
| 2007/0076217 A1 | 4/2007 | Baker et al. |
| 2007/0086013 A1 | 4/2007 | De Lega et al. |
| 2007/0086017 A1 | 4/2007 | Buckland et al. |
| 2007/0091317 A1 | 4/2007 | Freischlad et al. |
| 2007/0133002 A1 | 6/2007 | Wax et al. |
| 2007/0188855 A1 | 8/2007 | Shishkov et al. |
| 2007/0203404 A1 | 8/2007 | Zysk et al. |
| 2007/0208225 A1 | 9/2007 | Czaniera et al. |
| 2007/0223006 A1 | 9/2007 | Tearney et al. |
| 2007/0233056 A1 | 10/2007 | Yun |
| 2007/0233396 A1 | 10/2007 | Tearney et al. |
| 2007/0236700 A1 | 10/2007 | Yun et al. |
| 2007/0253901 A1 | 11/2007 | Deng et al. |
| 2007/0258094 A1 | 11/2007 | Izatt et al. |
| 2007/0263226 A1 | 11/2007 | Kurtz et al. |
| 2007/0291277 A1 | 12/2007 | Everett et al. |
| 2008/0002197 A1 | 1/2008 | Sun et al. |
| 2008/0007734 A1 | 1/2008 | Park et al. |
| 2008/0013960 A1* | 1/2008 | Tearney et al. ............... 398/139 |
| 2008/0021275 A1 | 1/2008 | Tearney et al. |
| 2008/0049220 A1 | 2/2008 | Izzia et al. |
| 2008/0070323 A1 | 3/2008 | Hess et al. |
| 2008/0094613 A1 | 4/2008 | de Boer et al. |
| 2008/0094637 A1 | 4/2008 | de Boer et al. |
| 2008/0097225 A1 | 4/2008 | Tearney et al. |
| 2008/0097709 A1 | 4/2008 | de Boer et al. |
| 2008/0100837 A1 | 5/2008 | de Boer et al. |
| 2008/0139906 A1 | 6/2008 | Bussek et al. |
| 2008/0152353 A1 | 6/2008 | de Boer et al. |
| 2008/0154090 A1 | 6/2008 | Hashimshony |
| 2008/0192236 A1 | 8/2008 | Smith et al. |
| 2008/0201081 A1 | 8/2008 | Reid |
| 2008/0204762 A1 | 8/2008 | Izatt et al. |
| 2008/0218696 A1 | 9/2008 | Mir |
| 2008/0226029 A1 | 9/2008 | Weir et al. |
| 2008/0228086 A1 | 9/2008 | Ilegbusi et al. |
| 2008/0234560 A1 | 9/2008 | Nomoto et al. |
| 2008/0252901 A1 | 10/2008 | Shimizu |
| 2008/0265130 A1 | 10/2008 | Colomb et al. |
| 2008/0297806 A1 | 12/2008 | Motachiannezam |
| 2008/0308730 A1 | 12/2008 | Vizi et al. |
| 2009/0004453 A1 | 1/2009 | Murai et al. |
| 2009/0005691 A1 | 1/2009 | Huang |
| 2009/0011948 A1 | 1/2009 | Uniu et al. |
| 2009/0012368 A1 | 1/2009 | Banik et al. |
| 2009/0044799 A1 | 2/2009 | Bangsaruntip et al. |
| 2009/0051923 A1 | 2/2009 | Andres et al. |
| 2009/0131801 A1 | 5/2009 | Suter et al. |
| 2009/0192358 A1 | 7/2009 | Yun |
| 2009/0196477 A1 | 8/2009 | Cense et al. |
| 2009/0209834 A1 | 8/2009 | Fine |
| 2009/0273777 A1 | 11/2009 | Yun et al. |
| 2009/0281390 A1 | 11/2009 | Quinjun et al. |
| 2009/0290156 A1 | 11/2009 | Popescu et al. |
| 2009/0305309 A1 | 12/2009 | Chien et al. |
| 2009/0306520 A1 | 12/2009 | Schmitt et al. |
| 2009/0323056 A1 | 12/2009 | Yun et al. |
| 2010/0002241 A1 | 1/2010 | Hirose |
| 2010/0086251 A1 | 4/2010 | Xu et al. |
| 2010/0094576 A1 | 4/2010 | de Boer et al. |
| 2010/0145145 A1 | 6/2010 | Shi et al. |
| 2010/0150467 A1 | 6/2010 | Zhao et al. |
| 2010/0261995 A1 | 10/2010 | Mckenna et al. |
| 2011/0028967 A1 | 2/2011 | Rollins et al. |
| 2011/0160681 A1 | 6/2011 | Dacey, Jr. et al. |
| 2011/0218403 A1 | 9/2011 | Tearney et al. |

FOREIGN PATENT DOCUMENTS

| | | |
|---|---|---|
| EP | 0697611 | 2/1996 |
| EP | 2149776 | 2/2010 |
| JP | 361040633 | 3/1986 |
| JP | 62-188001 | 6/1989 |
| JP | 04-056907 | 2/1992 |
| JP | 20040056907 | 2/1992 |
| JP | H8-136345 | 5/1996 |
| JP | H08-160129 | 6/1996 |
| JP | 9-10213 | 1/1997 |
| JP | 9-230248 | 9/1997 |
| JP | 10-213485 | 8/1998 |
| JP | 10-267631 | 10/1998 |
| JP | 10-267830 | 10/1998 |
| JP | 2259617 | 10/1999 |
| JP | 2000-023978 | 1/2000 |
| JP | 2000-046729 | 2/2000 |
| JP | 2000-121961 | 4/2000 |
| JP | 2000-504234 | 4/2000 |
| JP | 2000-126116 | 5/2000 |
| JP | 2000-131222 | 5/2000 |
| JP | 2001-4447 | 1/2001 |
| JP | 2001-500026 | 1/2001 |
| JP | 2001-104315 | 4/2001 |
| JP | 2001-174404 | 6/2001 |
| JP | 2001-174744 | 6/2001 |
| JP | 2001-507251 | 6/2001 |
| JP | 2001-508340 | 6/2001 |
| JP | 2007-539336 | 6/2001 |
| JP | 2001-212086 | 8/2001 |
| JP | 2008-533712 | 8/2001 |
| JP | 2001-264246 | 9/2001 |
| JP | 2001-515382 | 9/2001 |

(56) References Cited

FOREIGN PATENT DOCUMENTS

| | | |
|---|---|---|
| JP | 2001-525580 | 12/2001 |
| JP | 2002-503134 | 1/2002 |
| JP | 2002-035005 | 2/2002 |
| JP | 2002-205434 | 2/2002 |
| JP | 2002-095663 | 4/2002 |
| JP | 2002-113017 | 4/2002 |
| JP | 2002-148185 | 5/2002 |
| JP | 2002-516586 | 6/2002 |
| JP | 2002-214127 | 7/2002 |
| JP | 2002-214128 | 7/2002 |
| JP | 2003-014585 | 1/2003 |
| JP | 2003-504627 | 2/2003 |
| JP | 20030035659 | 2/2003 |
| JP | 2003-512085 | 4/2003 |
| JP | 2003-513278 | 4/2003 |
| JP | 2003-516531 | 5/2003 |
| JP | 2004-028970 | 1/2004 |
| JP | 2004-037165 | 2/2004 |
| JP | 2004-057652 | 2/2004 |
| JP | 2004-089552 | 3/2004 |
| JP | 2004-113780 | 4/2004 |
| JP | 2004-514920 | 5/2004 |
| JP | 2004-258144 | 9/2004 |
| JP | 2004-317437 | 11/2004 |
| JP | 2005-062850 | 3/2005 |
| JP | 2005-110208 | 4/2005 |
| JP | 2005-510323 | 4/2005 |
| JP | 2005-156540 | 6/2005 |
| JP | 2005-516187 | 6/2005 |
| JP | 2005-195485 | 7/2005 |
| JP | 2005-241872 | 9/2005 |
| JP | 2006-237359 | 9/2006 |
| JP | 2007-500059 | 1/2007 |
| JP | 2007-075403 | 3/2007 |
| JP | 2007-83053 | 4/2007 |
| JP | 2007-524455 | 8/2007 |
| JP | 2003-102672 | 4/2012 |
| RU | 2149464 | 5/2000 |
| RU | 2209094 | 7/2003 |
| RU | 2213421 | 9/2003 |
| RU | 2242710 | 12/2004 |
| RU | 2255426 | 6/2005 |
| RU | 2108122 | 6/2006 |
| WO | 1996-02184 | 2/1996 |
| WO | 1996-04839 | 2/1996 |
| WO | 1998-35203 | 8/1998 |
| WO | 99-28856 | 6/1999 |
| WO | 1999-45838 | 9/1999 |
| WO | 1999-45338 | 10/1999 |
| WO | 2000-42906 | 7/2000 |
| WO | 2000-43730 | 7/2000 |
| WO | 2001-04828 | 1/2001 |
| WO | 2001-033215 | 5/2001 |
| WO | 2001-38820 | 5/2001 |
| WO | 2001-42735 | 6/2001 |
| WO | 2001-82786 | 11/2001 |
| WO | 2002-037075 | 5/2002 |
| WO | 20020037075 | 5/2002 |
| WO | 2002-045572 | 6/2002 |
| WO | 2002-068853 | 6/2002 |
| WO | 2002-054027 | 7/2002 |
| WO | 2002-083003 | 10/2002 |
| WO | 2003-003903 | 1/2003 |
| WO | 2003-012405 | 2/2003 |
| WO | 2003-013624 | 2/2003 |
| WO | 20030013624 | 2/2003 |
| WO | 20030053226 | 7/2003 |
| WO | 03-088826 | 10/2003 |
| WO | 2003-088826 | 10/2003 |
| WO | 2004-037068 | 5/2004 |
| WO | 2004-043251 | 5/2004 |
| WO | 2004-073501 | 9/2004 |
| WO | 2004-100789 | 11/2004 |
| WO | 2004-105598 | 12/2004 |
| WO | 2005-045362 | 5/2005 |
| WO | 2005-047813 | 5/2005 |
| WO | 20050082225 | 9/2005 |
| WO | 2006-020605 | 2/2006 |
| WO | 20060038876 | 4/2006 |
| WO | 2006-050320 | 5/2006 |
| WO | 2006-058187 | 6/2006 |
| WO | 2006-131859 | 12/2006 |
| WO | 2007-030835 | 3/2007 |
| WO | 2009-033064 | 3/2009 |
| WO | 20090153929 | 12/2009 |
| WO | 2011-055376 | 5/2011 |
| WO | 2011-080713 | 7/2011 |

OTHER PUBLICATIONS

R.H. Hardwick et al., (1995) "c-erbB-2 Overexpression in the Dysplasia/Carcinoma Sequence of Barrett's Oesophagus," Journal of Clinical Pathology, vol. 48, No. 2, pp. 129-132.
W. Polkowski et al, (1998) Clinical Decision making in Barrett's Oesophagus can be supported by Computerized Immunoquantitation and Morphometry of Features Associated with Proliferation and Differentiation, Journal of pathology, vol. 184, pp. 161-168.
X. Qi et al., (2004) "Computer Aided Diagnosis of Dysphasia in Barrett's Esophagus Using Endoscopic Optical Coherence Tomovaphy," SPIE, Coherence Domain Optical Methods and Optical Coherence Tomography in Biomedicine VIII. Proc. of Conference on., vol. 5316, pp. 33-40.
Montag Ethan D., "Parts of the Eye" online textbook for JIMG 774: Vision & Psycophysics, download on Jun. 23, 2010 from http://www.cis.rit.edu/people/faculty/montag/vandplite/pages/chap_8/ch8p3.html.
Swan et al., "Toward Nanometer-Scale Resolution in Fluorescence Microscopy using Spectral Self-Inteference" IEEE Journal. Selected Topics in Quantum Electronics 9 (2) 2003, pp. 294-300.
Moiseev et al., "Spectral Self-Interference Fluorescence Microscopy", J. Appl. Phys. 96 (9) 2004, pp. 5311-5315.
Wojtkowski, Maciej, Ph.D. "Three-Dimensional Retinal Imaging with High-Speed Ultrahigh-Resolution Optical Coherence Tomography" Ophthalmology, Oct. 2005, 112(10): 1734-1746.
Hess, S.T. et al. "Ultra-high Resolution Imaging by Fluorescence Photoactivation Localization Microscopy" Biophysical Journal vol. 91, Dec. 2006, 4258-4272.
V. Tuchin et al., "Speckle interferometry in the measurements ofbiotissues vibrations," SPIE, 1647: 125 (1992).
Japanese Notice of Reasons for Rejection dated Dec. 12, 2011 for JP 2008-333712.
Japanese Notice of Reasons for Rejection dated Feb. 15, 2012 for JP 2008-553509.
Offce Action dated Jan. 25, 2013 for U.S. Appl. No. 11/537,043.
International Search Report dated Jan. 27, 2010 for PCT/US2009/050553.
International Search Report dated Jan. 27, 2010 for PCT/US2009/047988.
International Search Report dated Feb. 23, 2010 for U.S. Appl. No. 11/445,131.
Office Action dated Mar. 18, 2010 of U.S. Appl. No. 11/844,454.
Office Action dated Apr. 8, 2010 of U.S. Appl. No. 11/414,564.
Japanese Office Action dated Apr. 13, 2010 for Japanese Patent application No. 2007-515029.
International Search Report dated May 27, 2010 for PCT/US2009/063420.
Office Action dated May 28, 2010 for U.S. Appl. No. 12/015,642.
Office Action dated Jun. 2, 2010 for U.S. Appl. No. 12/112,205.
Office Action dated Jul. 7, 2010 for U.S. Appl. No. 11/624,277.
Office Action dated Jul. 16, 2010 for U.S. Appl. No. 11/445,990.
Office Action dated Jul. 20, 2010 for U.S. Appl. No. 11/625,135.
Office Action dated Aug. 5, 2010 for U.S. Appl. No. 11/623,852.
Chinese Office Action dated Aug. 4, 2010 for CN 200780005949.9.
Chinese Office Action dated Aug. 4, 2010 for CN 200780016266.3.
Office Action dated Aug. 27, 2010 for U.S. Appl. No. 11/569,790.
Office Action dated Aug. 31, 2010 for U.S. Appl. No. 11/671,278.
Office Action dated Sep. 3, 2010 for U.S. Appl. No. 12/139,314.
European Search Report dated Dec. 3, 2010 for EP 10182442.3.

(56) References Cited

OTHER PUBLICATIONS

Notice of Reasons for Rejection dated May 5, 2010 for JP 2006-515266.
Office Action dated Jun. 4, 2010 for U.S. Appl. No. 11/285,301.
Office Action dated Jun. 8, 2010 for U.S. Appl. No. 12/201,816.
Chinese Office Action dated Jun. 8, 2010 for Chinese application No. 200780031332.4.
Office Action dated Jun. 10, 2010 for U.S. Appl. No. 11/505,700.
European Office Action dated Jun. 11, 2010 for EP 07761877.5.
European Office Action dated Jul. 14, 2010 for EP 06751266.5.
Office Action dated Sep. 29, 2010 for U.S. Appl. No. 11/672,571.
International Search Report and Written Opinion dated Aug. 31, 2010 for PCT/US2010/022034.
Office Action dated Oct. 20, 2010 for U.S. Appl. No. 12/015,642.
Office Action dated Oct. 25, 2010 for U.S. Appl. No. 11/622,854.
Office Action dated Oct. 26, 2010 for U.S. Appl. No. 11/211,482.
Office Action dated Oct. 27, 2010 for U.S. Appl. No. 11/744,287.
Office Action dated Nov. 15, 2010 for U.S. Appl. No. 12/795,529.
Notice of Allowance and Fees dated Nov. 23, 2010 for U.S. Appl. No. 12/621,918.
Office Action dated Nov. 24, 2010 for U.S. Appl. No. 11/624,334.
Notice of Allowance and Fees dated Dec. 1, 2010 for U.S. Appl. No. 12/261,967.
Office Action dated Dec. 3, 2010 for U.S. Appl. No. 12/210,979.
International Search Report and Written Opinion dated Feb. 23, 2011 for PCT/US2010/041923.
Extended European Search Report dated Dec. 14, 2010 for EP 10132301.1.
International Search report dated Apr. 29, 2011 for PCT/US2010/051715.
International Search report dated Sep. 13, 2010 for PCT/US2010/023215.
International Search report dated Jul. 28, 2011 for PCT/US2010/059534.
International Search report dated Nov. 13, 2011 for PCT/US2011/027450.
International Search report dated Nov. 18, 2011 for PCT/US2011/027437.
International Search report dated Nov. 22, 2011 for PCT/US2011/027421.
R. Haggitt et al., "Barrett's Esophagus Correlation Between Mucin Histochemistry, Flow Cytometry, and Histological Diagnosis for Predicting Increased Cancer Risk," Apr. 1988, American Journal of Pathology, vol. 131, No. 1, pp. 53-61.
R.H. Hardwick et al., (1995) "c-erbB-2 Overexpression in the Dysplasia/Carcinoma Sequence of Barrett's Desophagus," Journal of Clinical Pathology, vol. 48, No. 2, pp. 129-132.
W. Polkowski et al, (1998) Clinical Decision making in Barret's Oesophagus can be supported by Computerized Immunoquantitation and Morphometry of Features Associated with Proliferation and Differentiation, Journal of pathology, vol. 184, pp. 161-168.
J.R. Turner et al., MN Antigen Expression in Normal Preneoplastic, and Neoplastic Esophagus: A Clinicopathological Study of a New Cancer-Associated Biomarker,: Jun. 1997, Human Pathology, vol. 28, No. 6, pp. 740-744.
D.J. Bowery et al., (1999) "Patterns of Gastritis in Patients with Gastro-Oesophageal Reflux Disease,", Gut, vol. 45, pp. 798-803.
O'Reich et al., (2000) "Expression of Oestrogen and Progesterone Receptors in Low-Grade Endometrial Stromal Sarcomas,", British Journal of Cancer, vol. 82, No. 5, pp. 1030-1034.
M.I. Canto et al., (1999) "Vital Staining and Barrett's Esophagus," Gastrointestinal Endoscopy, vol. 49, No. 3, Part 2, pp. S12-S16.
S. Jackle et al., (2000) "In Vivo Endoscopic Optical Coherence Tomography of the Human Gastrointestinal Tract-Toward Optical Biopsy," Enscopy, vol. 32, No. 10, pp. 743-749.
E. Montgomery et al., "Reproducibility of the Diagnosis of Dysplasia in Barrett Esophagus: A Reaffirmation," Apr. 2001, Human Pathology, vol. 32, No. 4, pp. 368-378.
H. Geddert et al., "Expression of Cyclin B1 in the Metaplasia-Dysphasia-Carcinoma Sequence of Barrett Esophagus," Jan. 2002, Cancer, vol. 94, No. 1, pp. 212-218.
P. Pfau et al., (2003) "Criteria for the Diagnosis of Dysphasia by Endoscopic Optical Coherence Tomography," Gastrointestinal Endoscopy, vol. 58, No. 2, pp. 196-2002.
R. Kiesslich et al., (2004) "Confocal Laser Endoscopy for Diagnosing Intraepithelial Neoplasias and Colorectal Cancer in Vivo," Gastroenterology, vol. 127, No. 3, pp. 706-713.
X. Qi et al., (2004) "Computer Aided Diagnosis of Dysphasia in Barrett's Esophagus Using Endoscopic Optical Coherence Tomography," SPIE, Coherence Domain Optical Methods and Optical Coherence Tomography in Biomedicine VIII. Proc. of Conference on., vol. 5316, pp. 33-40.
Seltzer et al., (1991) "160 nm Continuous Tuning of a MQW Laser in an External Cavity Across the Entire 1.3 μm Communications Window," Electronics Letters, vol. 27, pp. 95-96.
Office Action dated Jan. 25, 2010 for U.S. Appl. No. 11/537,048.
Office Action dated Mar. 18, 2010 for U.S. Appl. No. 11/844,454.
Montag Ethan D., "Parts of the Eye" online textbook for JIMG 774: Vision & Psychophysics, download on Jun. 23, 2010 from http://www.cis.rit.edu/people/faculty/montag/vandplite/pages/chap_8/ch8p3.html.
Zhang et al., "Full Range Polarization-Sensitive Fourier Domain Optical Coherence Tomography" Optics Express, Nov. 29, 2004, vol. 12, No. 24.
Office Action dated Aug. 31, 2010 for U.S. Appl. No. 11/677,278.
Yong Zhao et al: "Virtual Data Grid Middleware Services for Data-Intensive Science", Concurrency and Computation: Practice and Experience, Wiley, London, GB, Jan. 1, 2000, pp. 1-7, pp. 1532-0626.
Swan et al., "Toward Nanometer-Scale Resolution in Fluorescence Microscopy using Spectral Self-Interference" IEEE Journal. Selected Topics in Quantum Electronics 9 (2) 2003, pp. 294-300.
Moiseev et al., "Spectral Self-Interference Fluorescence Microscopy", J. Appl. Phys. 96 (9) 2004, pp. 5311-5315.
Hendrik Verschueren, "Interference Reflection Microscopy in Cell Biology", J. Cell Sci. 75, 1985, pp. 289-301.
Park et al., "Diffraction Phase and Fluorescence Microscopy", Opt. Expr. 14 (18) 2006, pp. 8263-8268.
Swan et al., "High Resolution Spectral Self-Interference Fluorescence Microscopy", Proc. SPIE 4621, 2002, pp. 77-85.
Sanchez et al., "Near-Field Fluorscence Microscopy Based on Two-Photon Excvitation with Metal Tips", Phys. Rev. Lett. 82 (20) 1999, pp. 4014-4017.
Wojtkowski, Maciej. Ph.D. "Three-Dimensional Retinal Imaging with High-Speed Ultrahigh-Resolution Optical Coherence Tomography" Ophthalmology, Oct. 2005, 112(10): 1734-1746.
Vaughan, J.M. et al., "Brillouin Scattering, Density and Elastic Properties of the Lens and Cornea of the Eye", Nature, vol. 284, Apr. 3, 1980, pp. 489-491.
Hess, S.T. et al. "Ultra-high Resolution Imaging by Fluorescence Photoactivation Localization Microscopy" Biophysical Journal vol. 91, Dec. 2006, pp. 4258-4272.
Fernandez-Suarez, M. et al., "Fluorescent Probes for Super-Resolution Imaging in Living Cells" Nature Reviews Molecular Cell Biology vol. 9, Dec. 2008.
Extended European Search Report dated Dec. 14, 2010 for EP 10182301.1.
S. Hell et al., "Breaking the diffraction resolution limit by stimulated-emission—stimulated-emission-depletion fluorescence microscopy," Optics Letters. 19:495 (1995) and Ground State Depletion (GSD).
S. Hell et al. "Ground-State-Depletion fluorescence microscopy—a concept for breaking the diffraction resolution limit," Applied Physics B. 60:780 (1994)) fluorescence microscopy, photo-activated localization microscopy (PALM).
E. Betzig et al. "Imaging intracellular fluorescent proteins at nanometer resolution," Science 313:1642 (2006), stochastic optical reconstruction microscopy (STORM).
M. Rust et al. "Sub-diffraction-limited imaging by stochastic optical reconstruction microscopy (STORM)," Nature Methods 3:783 (2006), and structured illumination microscopy (SIM).

(56) References Cited

OTHER PUBLICATIONS

B. Bailey et al. "Enhancement of Axial Resolution in Fluorescence Microscopy by Standing-Wave Excitation," Nature 366:44 (1993).
M. Gustafsson "Surpassing the lateral resolution limit by a factor of two using structured illumination microscopy," Journal of Microscopy 198:82 (2000).
M. Gustafsson "Nonlinear structured illumination microscopy: Wide-field fluorescence imaging with theoretically unlimited resolution," PNAS 102:13081 (2005)).
R. Thompson et al. "Precise nanometer localization analysis for individual fluorescent probes," Biophysical Journal 82:2775 (2002).
K. Drabe et al. "Localization of Spontaneous Emission in front of a mirror," Optics Communications 73:91 (1989).
Swan et al. "Toward nanometer-scale resolution in fluorescence microscopy using spectral self-interference," IEEE Quantum Electronics 9:294 (2003).
C. Joo, et al. "Spectral Domain optical coherence phase and multiphoton microscopy," Optics Letters 32:623 (2007).
Virmani et al., "Lesions from sudden coronary death: A comprehensive morphological classification scheme for atherosclerotic lesions," Arterioscler. Thromb. Vase. Bio., 20:1262-75 (2000).
Gonzalez, R.C. and Wintz, P., "Digital Image Processing" Addison-Wesley Publishing Company, Reading MA, 1987.
V. Tuchin et al., "Speckle interferometry in the measurements ofbiotissues vibrations," SPIE, 1647:125 (1992).
A.A. Bednov et al., "Investigation of Statistical Properties of Lymph Flow Dynamics Using Speckle-Microscopy," SPIE, 2981: 181-90 (1997).
Feng et al., "Mesoscopic Conductors and Correlations in Laser Speckle Patters" Science, New Series, vol. 251, No. 4994, pp. 633-639 (Feb. 8, 1991).
Lee et al., "The Unstable Atheroma," Arteriosclerosis, Thrombosis & Vascular Biology, 17:1859-67 (1997).
International Search report dated Nov. 18, 2011 for PCT/US2011/027450.
Bussey, J.G. et al., "Minimal-Access Fetal Surgery for Twin-to-Twin Transfusion Syndrome," Surgical Endoscopy, vol. 18, pp. 83-86, 2004.
Senat, Marie-Victoire et al., "Endoscopic Laser Surgery Versus Serial . . . ," The New England Journal of Medicine, vol. 351, pp. 136-144, Jul. 8, 2004.
Huber, Agnes et al., "Stage-Related Outcome in Twin-Twin Transfusion Syndrome . . . ," Obstetrics & Gynecology, vol. 108, No. 2, pp. 333-337, Aug. 2006.
Gardiner, Helena M. et al., "Twin-Twin Transfusion Syndrome . . . ," Circulation, vol. 107, pp. 1906-1911, 2003.
Ville, Yves et al., "Endoscopic Laser Coagulation in the Management of Severe . . . ," British Journal of Obstetrics and Gynaecology, vol. 105, pp. 446-453, Apr. 1998.
Cincotta, R.B. et al., "Long Term Outcome of Twin-Twin Transfusion Syndrome," Arch. Dis. Child Fetal Neonatal Ed., vol. 83, pp. F171-F176, 2000.
Machin, G.A. et al., "Doppler Sonographic Demonstration of Arterio-Venous Anastomosis . . . ," Ultasound Obstet. Gynecol., vol. 16, pp. 214-217, 2000.
Cavicchioni, O. et al., "Intrauterine Fetal Demise Following Laser Treatment in . . . ," An International Journal of Obstetrics and Gynaecology, pp. 590-594, Mar. 27, 2006.
Ohno, Y. et al., "The Value of Doppler Ultrasound in the Diagnosis . . . ," Arch. Gynecol Obstet, vol. 255, pp. 37-42, 1994.
Yun, Seok H. et al., "Comprehensive Volumetric Optical Micropscopy in Vivo," Nat. Med., vol. 12, No. 12, pp. 1429-1433, Dec. 2006.
Kienle, Alwin et al., "Why do Veins Appear Blue? A New Look at an Old Question," Applied Optics, vol. 35, No. 7, pp. 1151-1160, Mar. 1, 1996.
Roggan, Andre et al., "Optical Properties of Circulating Human Blood in the Wavelength . . . ," Journal of Biomedical Optics, vol. 4, No. 1, pp. 36-46, Jan. 1999.

Faber, D.J. et al., "Toward Assessment of blood Oxygen Saturation by Spectroscopic . . . ," Optics Letters, vol. 30, No. 9, pp. 1015-1017, May 1, 2005.
Vakoc, B. J. et al., "Elimination of Depth Degeneracy in Optical Frequency-Domain Imaging . . . ," Optic Letter, vol. 31, No. 3, pp. 362-364, Feb. 1, 2006.
Hongchen, Zhai et al., "Color-Image Retrival Based on Fuzzy Correlation," Information Sciences, vol. 47, No. 3, pp. 295-300, 2004.
Bajoria, Rekha "Vascular Anatomy of Monochorionic Placenta in Relation to Discordant . . . ," Human Reproduction, vol. 13, No. 10, pp. 2933-2940, 1998.
Notice of Reasons for Rejection dated Nov. 2, 2011 for JP 2008-509233.
Notice of Reasons for Rejection dated Nov. 21, 2011 for JP 2007-525075.
Extended European Search Report dated Nov. 28, 2011 for EP 09767845.2.
International Search Report and Written Opinion for PCT/US2011/037916 dated Dec. 27, 2011.
International Search Report and Written Opinion for PCT/US2011/039066 dated Dec. 28, 2011.
Communication pursuant to Article 94(3) for EP 10186189.6 dated Dec. 22, 2011.
International Search Report and Written Opinion for PCT/US2011/038421 dated Jan. 12, 2012.
Japanese Language Appeal Decision dated Jan. 10, 2012 for JP 2006-503161.
Japanese Notice of Grounds for Rejection dated Oct. 28, 2011 for JP2009-294737.
Japanese Notice of Grounds for Rejection dated Dec. 28, 2011 for JP2008-535793.
Japanese Notice of Reasons for Rejection dated Dec. 12, 2011 for JP2003516531.
International Search Report and Written Opinion dated Feb. 9, 2012 based on PCT/US2011/034810.
European Search Report dated Mar. 2, 2012 for EP 11188120.7.
Japanese Notice of Reasons for Rejection dated Feb. 17, 2012 for JP 2007-539336.
Japanese Notice of Reasons for Rejection dated Feb. 15, 2012 for JP 20025-553509.
Japanese Notice of Reasons for Rejection dated Mar. 27, 2012 for JP 2008-554495.
Japanese Notice of Reasons for Rejection dated May 8, 2012 for JP 2008-533727.
Korean Office Action dated May 25, 2012 for KR 10-2007-7008116.
International Search Report and Written Opinion dated May 29, 2012 for PCT/US2011/058110.
International Search Report and Written Opinion dated May 29, 2012 for PCT/US2011/05007.
Japanese Notice of Reasons for Rejection dated Mar. 13, 2012 for JP2009-063553.
Japanese Notice of Reasons for Rejection dated May 21, 2012 for JP 2008-551523.
Japanese Notice of Reasons for Rejection dated Jun. 20, 2012 for JP 2099-546534.
Japanese Notice of Reasons for Reiection dated Jun. 26, 2012 for JP 2002-585939.
European Official Action dated Aug. 1, 2012 for EP 10193526.0.
European Search Report dated Jun. 25, 2012 for EP 10733985.5.
European Communication Pursuant to EPC Article 94(3) for EP 07845206.7 dated Aug. 30, 2012.
International Search Report and Written Opinion dated Aug. 30, 2012 for PCT/US2012/035234.
International Search Report and Written Opinion dated Aug. 16, 2012 for PCT/US2012/035887.
Japanese Notice of Reasons for Rejections dated Oct. 10, 2012 for 2008-553511.
Japanese Notice of Reasons for Rejections dated Oct. 2, 2012 for 2007-543626.
Canadian Office Action dated Oct. 10, 2012 for 2,514,189.

(56) References Cited

OTHER PUBLICATIONS

Japanese Notice of Reasons for Rejections dated Nov. 9, 2012 for 2007-530134.
Japanese Notice of Reasons for Rejection dated Nov. 27, 2012 for 2009-554772.
Japanese Notice of Reasons for Rejection dated Oct. 11, 2012 for 2008-533712.
Japanese Notice of Reasons for Rejection dated Dec. 18, 2012 for 2011-136398.
International Search Report and Written Opinion dated Oct. 25, 2012 for PCT/US2012/047415.
International Search Report and Written Opinion dated Aug. 16, 2012 for PCT/US2012/051132.
European Official Communication dated Feb. 11, 2013 for EP 08837490.5.
European Official Communication dated Feb. 15, 2012 for EP 04822169.1.
International Search Report dated Jan. 31, 2013 for PCT/US2012/061135.
Internatioual Search Report and Written Opinion dated Jan. 31, 2013 for PCT/US2012/060843.
European Search Report dated Mar. 11, 2013 for EP 10739129.4.
Notice of Reasons for Rejection dated Feb. 5, 2013 for JP 2008-509233.
Notice of Reasons for Rejection dated Feb. 19, 2013 for JP 2008-507983.
European Extended Search Report dated Mar. 26, 2013 for EP 09825421.1.
International Search Report and Written Opinion dated Dec. 6, 2012 for PCT/US2012/052553.
European Extended Search Repon dated Feb. 1, 2013 for EP 12171521.3.
Official European Search report dated Apr. 24, 2013 for EP 10182341.7.
Notice of Reasons for Rejection dated Apr. 16, 2013 for JP 2008-533727.
Notice of Reasons for Rejection dated Apr. 16, 2013 for JP 2009-510092.
Notice of Reasons for Rejection dated May 7, 2013 for JP 2011-508674.
European Search Report for 12194876.4 dated Feb. 1, 2013.
Japanese Notice of Reasons for Rejection for 2010-529142 dated Jan. 29, 2013.
Japanese Notice of Reasons for Rejection for 2007-539336 dated May 21, 2013.
International Search Report and Written Opinion for PCT/US2013/022136.
European Official Communication dated Jun. 28, 2013 for EP 09158713.9.
Japanese Notice of Reasons for Rejection for 2013-026897 dated Jun. 6, 2013.
Japanese Notice of Reasons for Rejection for 2013-026880 dated Jun. 6, 2013.
International Application Search Report and Written Opinion dated Apr. 11, 2013 for PCT/US2013/021299.
Extended European Search Report dated Jul. 2, 2013 for EP 10738929.8.
European Search Report dated Jul. 15, 2013 for EP 10800455.7.
European Search Report dated Jul. 26, 2013 for EP 09743687.7.
Extended European Search Repon dated Jul. 11, 2013 for EP 09832543.4.
Japanese Office Action dated Aug. 20, 2013 for JP 2011-546443.
International Search Report and Written Opinion dated Sep. 19, 2013 for PCT/US2013/042008.
Japanese Notice of Reasons for Rejection dated Jul. 16, 2013 for JP 2009-063553.
Korean Notification of Ground for Rejection dated Sep. 30, 2013 for 10-2007-7027721.
European Search Report dated Sep. 10, 2013 for EP 10183412.5.
Japanese Official Action dated Oct. 15, 2013 for JP 2012-181098.
Japanese Office Action dated Oct. 8, 2013 for JP 2011-168738.
Poneros er al: "Optical Coherence Tomography of the Biliary Tree During ERCP", Gastrointestinal Endoscopy, Elsevier, NL, vol. 55, No. 1, Jan. 1, 2002, pp. 84-88.
Fu L et tal: Double-Clad Photonic Crystal Fiber Coupler for compact Nonlinear Optical Microscopy Imaging, Optics Letters, OSA, Optical Society of America, vol. 31, No. 10, May 15, 2006, pp. 1471-1473.
Japanese Notice of Reasons for Rejection dated Dec. 12, 2011 for JP 2008-533712.
Japanese Notice of Reasons for Rejection dated Mar. 27, 2012 for JP 2003-102672.
Japanese Notice of Reasons for Rejection dated Jun. 20, 2012 for JP 2009-546534.
European Official Communication dated Aug. 1, 2012 for EP 10193526.0.
Wieser, Wolfgang et al., "Multi-Megahertz OCT: High Quality 3D Imaging at 20 million A-Scans and 4.5 Gvoxels Per Second" Jul. 5, 2010, vol. 18, No. 14, Optics Express.
Giuliano Scarcelli et al., "Three-Dimensional Brillouin Confocal Microscopy". Optical Society of American, 2007, CtuV5.
Giuliano, Scarcelli et al., "Confocal Brillouin Microscopy for Three-Dimensional Mechanical Imaging." Nat Photonis, Dec. 9, 2007.
Japanese Notice of Reasons for Rejections dated Oct. 10, 2012 for 2008-553511 PO.
W.Y. Oh et al: "High-Speed Polarization, Sensitive Optical Frequency Domain Imaging with Frequency Multiplexing", Optics Express, vol. 16, No. 2, Jan. 2008.
Athey, B.D. et al., "Development and Demonstration of a Networked Telepathology 3-D Imaging, Databasing, and Communication System", 1998 ("C2"), pp. 5-17.
D'Amico, A. V., et al., "Optical Coherence Tomography as a Method for Identifying Benign and Maliganat Microscopic Structures in the Prostate Gland", Urology, vol. 55, Isue 5, May 2000 ("C3"), pp. 783-787.
Tearney, G.J. et al., "In Vivo Endoscopic Optical Biopsy with Optical Coherence Tomography", Science, vol. 276, No. 5321, Jun. 27, 1997 ("C6"), pp. 2037-2039.
Japanese Notice of Reasons for Rejections dated Nov. 9, 2012 for JP 2007-530134.
Japanese Notice of Reasons for Rejections dated Nov. 27, 2012 for JP 2009-554772.
Japanese Notice of Reasons for Rejections dated Oct. 11, 2012 for JP 2008-533712.
Yoden, K. et al. "An Approach to Optical Reflection Tomography Along the Geometrial Thickness," Optical Review, vol. 7, No. 5, Oct. 1, 2000.
Joshua, Fox et al: "Measuring Primate RNFL Thickness with OCT", IEEE Journal of Selected Topics in Quantum Electronics, IEEE Service Center, Piscataway, NJ, US, vol. 7,No. 6, Nov. 1, 2001.
European Official Communication dated Feb. 6, 2013 for 04822169.1.
Viliyam K. Pratt. Lazernye Sistemy Svyazi. Moskva, Izdatelstvo "Svyaz", 1972. p. 68-70.
International Search Report and Written Opinion dated Jan. 31, 2013 for PCT/US2012/060843.
European Search Report dated Mar. 11, 2013 doe EP 10739129.4.
Huber, R et al: "Fourier Domain Mode Locked Lasers for OCT Imaging at up to 290 kHz Sweep Rates", Proceedings of SPIE, SPIE—International Society for Optical Engineering, US, vol. 5861, No. 1, Jan. 1, 2005.
M. Kourogi et al: "Programmable High Speed (1MHz) Vernier-mode-locked Frequency-Swept Laser for OCT Imaging", Proceedings of SPIE, vol. 6847, Feb. 7, 2008.
Masahiro, Yamanari et al: "polarization-Sensitive Swept-Source Optical Coherence Tomography with Continuous Source Polarization Modulation", Optics Express, vol. 16, No. 8, Apr. 14, 2008.
European Extended Search Report dated Feb. 1, 2013 for EP 12171521.3.
Nakamura, Koichiro et al., "A New Technique of Optical Ranging by a Frequency-Shifted Feedback Laser", IEEE Phontonics Technology Letters, vol. 10, No. 12, pp. 1041-1135, Dec. 1998.

(56) References Cited

OTHER PUBLICATIONS

Lee, Seok-Jeong et al., "Ultrahigh Scanning Speed Optical Coherence Tomography Using Optical Frequency Comb Generators", The Japan Soceity of Applied Physics, vol. 40 (2001).
Kinoshita, Masaya et al., "Optical Frequency-Domain Imaging Microprofilmetry with a Frequency-Tunable Liquid-Crystal Fbry-Perot Etalon Device" Applied Optics, vol. 38, No. 34, Dec. 1, 1999.
Bachmann A.H. et al: "Heterodyne Fourier Domain Optical Coherence Tomography for Full Range Probing with High Axial Resolution", Optics Express, OSA, vol. 14, No. 4, Feb. 20, 2006.
Thomas J. Flotte: "Pathology Correlations with Optical Biopsy Techniques", Annals of the New York Academy of Sciences, Wiley-Blackwell Publishing, Inc. SU, vol. 838, No. 1, Feb. 1, 1998, pp. 143-149.
Constance R. Chu et al: Arthroscopic Microscopy of Articular Cartilage Using Optical Coherence Tomography, American Journal of Sports Medicine, American Orthopedic Society for Sports Medicine, Waltham, MA, Vo. 32, No. 9, Apr. 1, 2004.
Bouma B E et al: Diagnosis of Specialized Intestinal Metaplasia of the Esophagus with Optical Coherence Tomography, Conference on Lasers and Electro-Optics. Technical Digest. OSA, US, vol. 56, May 6, 2001.
Shen et al: "Ex Vivo Histology-Correlated Optical Coherence Tomography in the Detection of Transmural Inflammation in Crohn's Disease", Clinical Gastroenterology and Heptalogy, vol. 2, No. 9, Sep. 1, 2004.
Shen et al: "In Vivo Colonscopic Optical Coherence Tomography for Transmural Inflammation in Inflammatory Bowel Disease", Clinical Gastroenterology and Hepatology, American Gastroenterological Association, US, vol. 2, No. 12, Dec. 1, 2004.
Ge Z et al: "Identification of Colonic Dysplasia and Neoplasia by Diffuse Reflectance Spectroscopy and Pattern Recognition Techniques", Applied Spectroscopy, The Society for Applied Spectroscopy, vol. 52, No. 6, Jun. 1, 1998.
Elena Zagaynova et al: "Optical Colierence Tomography: Potentialities in Clinical Practice", Proceedings of SPIE, Aug. 20, 2004.
Westphal et al: "Correlation of Endoscopic Optical Coherence Tomography with Histology in the Lower-GI Tract", Gastrointestinal Endoscopy, Elsevier, NL, vol. 61, No. 4, Apr. 1, 2005.
Haggitt et al: "Barrett's Esophaagus, Dysplasia, and Adenocarcinoma", Human Pathology, Saunders, Philadelphia, PA, US, vol. 25, No. 10, Oct. 1, 1994.
Gang Yao et al. "Monte Carlo Simulation of an Optical Coherence Tomography Signal in Homogenous Turbid Media," Physics in Medicine and Biology, 1999.
Murakami, K. "A Miniature Confocal Optical Scanning Microscopy for Endscopes", Proceedings of SPIE, vol. 5721, Feb. 28, 2005, pp. 119-131.
Seok, H. Yun et al: "Comprehensive Volumetric Optical Microscopy in Vivo", Nature Medicine, vol. 12, No. 12, Jan. 1, 2007.
Baxter: "Image Zooming", Jan. 25, 2005, Retrieved from the Internet.
Qiang Zhou et al: "A Novel Machine Vision Application for Analysis and Visualization of Confocal Microscopic Images" Machine Vision and Applications, vol. 16, No. 2, Feb. 1, 2005.
Igor Gurov et al: (2007) "Full-field High-Speed Optical Coherence Tomography System for Evaluting Multilayer and Random Tissues", Proc. of SPIE, vol. 6618.
Igor Gurov et al: "High-Speed Signal Evaluation in Optical Coherence Tomography Based on Sub-Nyquist Sampling and Kalman Filtering Method" AIP Coherence Proceedings, vol. 860, Jan. 1, 2006.
Groot De P et al: "Three Dimensional Imaging by Sub-Nyquist Sampling of White-Light Interferograms", Optics Letters, vol. 18, No. 17, Sep. 1, 1993.
Silva et al: "Extended Range, Rapid Scanning Optical Delay Line for Biomedical Interferometric Imaging", Electronics Letters, IEE Stevenage, GB vol. 35, No. 17, Aug. 19, 1999.

\* cited by examiner

APPARATUS AND METHOD FOR OBTAINING AND PROVIDING IMAGING INFORMATION ASSOCIATED WITH AT LEAST ONE PORTION OF A SAMPLE, AND EFFECTING SUCH PORTION(S)

CROSS-REFERENCE TO RELATED APPLICATION(S)

This application is a divisional application of, and therefore claims priority from, U.S. patent application Ser. No. 11/875,676, filed on Oct. 19, 2007 and from U.S. Patent Application Ser. No. 60/862,205 filed on Oct. 19, 2006, the entire disclosures of which are incorporated herein by reference.

FIELD OF THE INVENTION

The present invention relates generally apparatus and method for providing imaging information associated with at least one portion of a sample, obtaining diagnostic information for a sample and/or modifying at least one property of at least one portion of the sample.

BACKGROUND INFORMATION

A concept of microendoscopy has been described for minimally invasive therapy in medicine. Small sizes of these devices can reduce anesthesia requirements and minimize tissue damage, opening up the possibility of safer intervention. Ultraminiature endoscopes may also give rise to new procedures, permitting diagnosis and microsurgery in previously inaccessible areas of the body. Previously, however, a widespread adoption of microendoscopy may be hampered by the poor image quality of current devices and the overall size of the endoscope and its associated microsurgical instrumentation. One of the objects of the present invention is to provide a new form of microendoscopically-guided therapy that overcomes these limitations.

Operative Fetoscopy.

Endoscopically-guided fetal surgery is one of the applications of microendoscopy.[4,5] Indications for intervention can include congenital diaphragmatic hernia, lower urinary tract obstruction, sacrococcygeal teratoma, and thoracic space occupying lesions, among others.[5,6] Placental surgery, notably laser coagulation of vessels on the chorionic plate, has gained significant attention for the treatment of twin-twin transfusion syndrome (TTTS).[7-13] The use of these techniques can result in live, healthy births in cases that would otherwise result in in utero fetal demise (IUFD).

Twin-Twin Transfusion Syndrome.

TTTS is considered a complication of monochorionic pregnancies where blood is preferentially shunted through placental arteriovenous (A-V) anastomoses towards one twin and away from the other. In severe TTTS, the donor twin becomes hypovolemic, resulting in oligohydramnios and oliguria.[2] The recipient twin conversely becomes hemodynamically overloaded, with subsequent polyhydramnios and polyuria.[2] Severe TTTS can occur in 15% of monochorionic pregnancies, at a rate of approximately 3000/year in the United States.[2] When left untreated, organ and cardiac failure ensue, resulting in mortality rates ranging from 80-90%, with significant neurological defects in surviving twins.[2,14]

Laser Coagulation for Treatment of TTTS.

A variety of treatments for TTTS have been investigated, including serial amnioreduction, septostomy, and fetoscopically-guided laser coagulation of placental A-V anastomoses.[2-4,15] Studies have shown that laser coagulation of communicating vessels appears to be the most promising of these techniques.[3,15] Laser coagulation therapy of TTTS can use a microendoscope, containing an instrumentation port, which is inserted through a cannula into the amnionic cavity. Generally, the amniotic fluid is replaced with warmed, sterile normal saline or Hartmann's solution to facilitate visualization.[1] Placental A-V anastomoses may be identified using the fetoscope by their characteristic anatomy, which can comprises an artery from one twin and a vein from the other, diving through a common foramen in the chorionic plate (as shown in FIG. 1A).[16] A 100-400 µm optical fiber is then inserted into the accessory port. The anastomotic vessels are coagulated using 0.1 sec pulses of 40-100 W light provided by a diode or Nd:YAG laser (1064 nm) delivered through the optical fiber (see FIG. 1B).[1] Multiple trials have shown that fetal survival is significantly improved when the laser coagulation is conducted prior to 26 weeks gestation, with an overall survival rate ranging from 55-72%.[2,3,7]

Potential Issues with Laser Coagulation.

While overall survival is significantly improved with laser coagulation, acute fetal loss due to an iatrogenic preterm premature rupture of membranes (iPPROM) can occur in greater than about 10% of cases.[4,12,17] This difficulty can be referred to as the "Achilles heel" of fetoscopic surgery.[1,4,5] One of the primary factors implicated in this high rate of fatal complications is the size of currently available fetoscopically-guided surgical instrumentation.[1,4,5] Conventional fetoscopes may have a diameter of 2.0 mm (see Karl Storz model 11630) and with the optical fiber for therapy, generally uses a 3.3 mm trocar for insertion into the amniotic sac.[3] In comparison, 22-gauge amniocentesis needles (~0.71 mm outer diameter) are generally associated with an iPPROM and fetal loss rate of <1%.[18-21] The size of current instrumentation should be significantly reduced to avoid the unacceptably high complication rates associated with the use of current fetoscopy technology.[1,4,5]

Other than iPPROM, improvements in identifying culprit vessels can decrease the number of adverse perinatal outcomes following therapy. Recent studies have shown that in many laser coagulation cases with neonatal hematologic complications, recurrent TTTS, IUFD, and adverse neurological outcomes, culprit vessels were not identified fetoscopically, and the coagulation of communicating vessels was incomplete.[22-25] The use of complementary procedures for visualizing blood flow, such as Doppler ultrasound,[26-28] has recently been proposed to increase knowledge of the pathophysiology of TTTS and potentially provide additional diagnostic parameters to guide the therapeutic procedure. Additionally, development of further fetoscope technology can be beneficial to provide higher quality images and new diagnostic information. Progress in these areas will undoubtedly increase the probability of identifying more communicating vessels, which in turn would likely increase the efficacy of laser coagulation therapy.

Microendoscope Technology.

Fetoscopes can be constructed from fiber-optic imaging bundles, which transmit two-dimensional images from the amnionic cavity to the physician.[1-3,5] Maintaining a good image quality with small diameter bundles is challenging; each optical fiber including its cladding has a finite diameter and only a limited number of optical fibers can be packed into a confined space. Small-diameter fiber bundles therefore provide images with a relatively low number of pixels. Single-mode fiber bundles, containing ultrathin fibers, have the highest fiber density. However these bundles are quite rigid and tend to have relatively low light throughput due to the cladding required on the optical fibers. Because the cladding does not transmit image data, pixelation artifact is also a problem, likely resulting in a honeycomb pattern superimposed on the image. The limitations of fiber bundles for miniature endoscopic imaging have motivated the search for other methods. Image formation with a single optical fiber is particularly attractive since single optical fibers are flexible and have excellent light transmission. There has been an attempt to rapidly scan light from a single fiber or the entire fiber itself to obtain an image.[29-31] While images devoid of pixelation artifacts, have been obtained using these techniques, the size of the scanning mechanisms can prohibit their use in the smallest endoscopes.

Spectrally-Encoded Endoscopy.

Another exemplary procedure has been developed for microendoscopy, which can be identified as spectrally-encoded endoscopy (SEE).[32] SEE can likely overcome the limitations of prior fiber-bundle fetoscopes for safer and more effective TTTS laser coagulation therapy. With SEE, e.g., a broadband light emanating from a fiber 200 can be separated into different colors (e.g., wavelengths) 210 using a lens/grating pair 220 at the distal end of the probe (as shown in FIG. 2). This exemplary optical configuration can focus each color onto a different location on the tissue, as illustrated in FIG. 2. Reflected light, returned back through the optics and fiber, can then be decoded outside of the body, using a spectrometer, to form one line of the endoscopic image. Such "fast-axis" of image acquisition can be performed remotely from the probe at rates ranging from 10-30 kHz. A two-dimensional image may be formed by moving the fiber using well-established mechanical devices, such as a motor or galvanometer that also reside outside the body.[33] Such second, "slow-axis" of scanning can be performed at a 30 Hz video rate. Since a high-speed scanning mechanism is not needed inside the endoscope, the diameter of the SEE probe can be as small as that of the optical fiber, which can typically be sized in the range of 80-250 µm. Furthermore, the number of pixels in an SEE image can be larger than that of fiber bundles, dependent on the spectral width of the light source and the ability of the probe to separate out the different wavelength components.

Spectral encoding is not only provided for a two-dimensional endoscopy. For example, when the grating and lens are placed in one arm of an optical interferometer, such procedure can also provide depth information. Three-dimensional imaging can be obtained using spectral encoding with a variety of interferometric techniques, including. e.g., speckle pattern subtraction and time-domain heterodyne interferometry.[34,35]

OBJECTS AND SUMMARY OF EXEMPLARY EMBODIMENTS

One of the objects of the present invention is to provide an ultraminiature (e.g., 350 µm diameter) endoscopic imaging apparatus/device/arrangement/system with integrated laser therapy capabilities for microsurgical applications inside the body, e.g., for safe and effective treatment of twin-twin transfusion syndrome (TTTS). It is possible to overcome the limitations and deficiencies of the current TTTS therapy devices by providing a much smaller microsurgical endoscope that provides more informative images with a better image quality. This exemplary enhancement includes spectrally encoded endoscopy (SEE) concepts that use wavelength division multiplexing to obtain high-resolution images through a single optical fiber. The exemplary SEE system and probe can be provided for color differentiation of arterial and venous placental vessels and can add Doppler imaging to quantify blood flow. Additionally, it is possible to incorporate therapeutic laser delivery through the same probe without increasing its size. exemplary total diameter of the exemplary apparatus/device/system/arrangement can be, e.g., 350 µm, small enough to be introduced into the amniotic cavity through an amniocentesis needle (e.g., 22-gauge), which can provide, e.g., a 10-fold reduction in complication rate.

Simultaneous imaging with more than one wavelength band can provide color information from the sample. One such exemplary embodiment of apparatus and method to achieve such exemplary result may include a coupling of visible (VIS) and near-infrared (NIR) light into the SEE fiber. If wavelengths are chosen correctly, for example 1064 and 532 nm, then the wavelength regions can overlap one another by diffracting at different orders. In another exemplary embodiment, the wavelengths may be selected such that the absorption properties of the sample can facilitate the differentiation and quantification of compounds within the sample, such as differentiation of arterial from venous blood by measuring differences in oxy- and deoxy-hemoglobin absorption. In yet another exemplary embodiment, the SEE probe may be situated in an interferometer, and a spectral interferometric phase may be detected and analyzed to provide information on blood flow and other motions of the sample. In another exemplary embodiment, the SEE probe may be configured by use of a specialty fiber or at least one fiber adjacent to the imaging fiber to deliver therapeutic light to the sample to effect therapy. In yet another exemplary embodiment, the delivery of therapy light may be conducted in parallel with an imaging procedure.

In still another exemplary embodiment, a small (e.g., 350 µm or other such diameter <2.0 mm) diameter SEE probe can utilize a dual-clad fiber; and the imaging light may be transmitted via a single-mode core. The therapy procedure can be performed via the innermost cladding. For example, a 1500 lines/mm grating can be used to provide two-dimensional imaging with greater than 90,000 pixels.

According to still another exemplary embodiment, the SEE-guided therapy probe can be configured to effect coagulation of blood vessels such as those of the placenta. In yet another exemplary embodiment, the SEE-guided therapy probe can be provided such that its diameter does not cause undue damage to the amniotic membranes or the uterus, so to facilitate a safe therapy and place the fetus and mother at minimal risk. According to a further exemplary embodiment, the size of the SEE probe can be sufficiently small to fit within a narrow gauge needle, for example with a gauge of 18-25 Ga. In a still further exemplary embodiment, the needle can be an amniocentesis needle.

Accordingly, with at least the above-described exemplary embodiments, a SEE-guided placental vascular coagulation procedure can be important for a care treatment for TTTS.

Further, according to yet another exemplary embodiment of the present invention, an ultraminiature endoscope with an integrated laser therapy system can be provided. One exemplary application of such device can include but not limited to, e.g., a treatment of twin-twin transfusion syndrome (TTTS), a serious complication of monochorionic twin pregnancies that occurs at a rate of 3000/year in the United States. In TTTS, communicating placental vessels shunt blood from one twin to the other, resulting in a very high fetal mortality rate and significant morbidity for survivors. Complete laser coagulation of the anastomotic vessels in utero can be an effective therapy for this disease. Prior operative fetoscopes are generally too large (e.g., 2-3 mm diameter), which can cause undue membrane damage when introduced into the amniotic cavity. Consequently, a placental laser therapy can be associated with unacceptable rates (10%) of iatrogenic preterm premature rupture of membranes (iPPROM) and in utero fetal demise (IUFD). The poor image quality of today's fetoscopes is also of concern, as incomplete coagulation due to missed anastomoses can lead to adverse perinatal outcomes following the laser therapy.

The exemplary embodiments of the present invention can overcome the deficiencies of the prior TTTS laser coagulation devices by being significantly smaller and by facilitating further options for identifying communicating vessels. This can be done using, e.g., spectrally encoded endoscopy (SEE) procedures and systems. SEE procedures and systems can use wavelength-division multiplexing to obtain high-resolution two- and three-dimensional endoscopic images through a single optical fiber. High-resolution, 3D video-rate imaging in vivo using a 350 μm diameter, monochromatic version of the SEE probe can be achieved with such procedures and systems. According to still other exemplary embodiments of the present invention, it is possible to obtain color imaging, and the exemplary device may provide a measurement blood flow. In yet another embodiment of the present invention, a therapeutic laser light may be coupled through the same fiber so that imaging and intervention can be accomplished concurrently without increasing the endoscope diameter.

For example, the size of the exemplary device can be, e.g., about 350 μm, so as to allow this device to be inserted into the amniotic cavity through a 22-gauge amniocentesis needle, which should lower the complication rates of placental laser therapy by an order of magnitude. Such exemplary embodiment of the device may facilitate a use thereof in other procedures where small size and highly capable image guided intervention can decrease complication rates and improve patient care.

According to a further exemplary embodiment of the present invention, the SEE procedures and apparatus can be utilized as follows. In particular, it is possible to provide a multifunctional SEE system and probe for discriminating arteries from veins. By incorporating high quality two- and three-dimensional imaging, e.g., color information and Doppler blood flow mapping, this exemplary device/system/arrangement/apparatus can be used to identify A-V anastomoses. Further, it is possible to transmit high power Nd:YAG laser light through the SEE probe to enable image-guided vessel photocoagulation without increasing the probe's size. Taken together, these exemplary features can facilitate the TTTS management to be enhanced by providing an endoscopic therapy system and apparatus with enhanced capabilities that can be inserted through an amniocentesis needle. This exemplary enhancement can make laser coagulation therapy for TTTS safer and more effective. In addition to a treatment of TTTS, this exemplary device/apparatus can be used for an endoscopically-guided therapy in other areas of the body that have previously been difficult to access.

In a further exemplary embodiment according to the present invention, the apparatus can be utilized to effect therapy for other applications. For example, if the therapy laser is designed to provide maximum absorption for water (e.g., around water absorption peaks at approximately 1500 nm, 1800 nm, 3000 nm, etc.), other therapy may be affected, such as tissue coagulation, ablation, etc. In addition or alternatively, according to another exemplary embodiment of the present invention, if an eximer laser or $CO_2$ laser is utilized in conjunction with the exemplary apparatus, such exemplary combination may be used for resurfacing or a superficial ablation.

Further, to address some of the objects of the present invention and/or deficiency with the conventional procedures and devices described herein, another exemplary embodiment of the apparatus according to the present invention can be provided. In particular, such exemplary apparatus . . . .

According to further exemplary embodiments of the present invention, apparatus and process can be provided for imaging information associated with at least one portion of a sample. For example, (i) at least two first different wavelengths of at least one first electro-magnetic radiation can be provided within a first wavelength range provided on the portion of the sample so as to determine at least one first transverse location of the portion, and (ii) at least two second different wavelengths of at least one second electro-magnetic radiation are provided within a second wavelength range provided on the portion so as to determine at least one second transverse location of the portion. The first and second ranges can east partially overlap on the portion. Further, a relative phase between at least one third electro-magnetic radiation electro-magnetic radiation being returned from the sample and at least one fourth electro-magnetic radiation returned from a reference can be obtained to determine a relative depth location of the portion. First information of the portion based on the first transverse location and the relative depth location, and second information of the portion based on the second transverse location and the relative depth location can be obtained. The imaging information may include the first and second information.

In addition, further information can be generated for the portion by combining the first and second information. At least two third different wavelengths of at least one fifth electro-magnetic radiation can be provided within a third wavelength range on the portion of the sample so as to determine at least one third transverse location of the portion Further, third information of the portion can be provided based on the third transverse location and the relative depth location, wherein the imaging information includes the third information. The first information can be associated with a red wavelength range, the second information may be associated with a green wavelength range, and the third information can be associated with a blue wavelength range. The imaging information can be three-dimensional information.

According to a stiff further exemplary embodiment of the present invention, apparatus and process can provide imaging information associated with at least one portion of the sample. For example, at least one wavelength of at least one particular electro-magnetic radiation can be provided on the portion of the sample so as to determine at least one transverse location of the portion. In addition, obtain a relative phase can be obtained between at least one first electro-magnetic radiation electro-magnetic radiation being returned from a sample and at least one second electro-magnetic radiation returned from a reference to determine a motion of the portion or of particles within or on the portion. The information of the portion can be provided based on the transverse location and the motion. A relative depth location of the portion can be determined, and the information may be provided as a further function of the relative depth location.

In yet another exemplary embodiment of the present invention, an apparatus for obtaining diagnostic information for a structure and modifying at least one property of at least one portion of the structure can be provided. For example, the apparatus can include a fiber configured to provide there through the electro-magnetic radiation. At least one first waveguiding portion of the fiber can be configured to provide a first electro-magnetic radiation to the portion so as to obtain the information, and at least one second waveguiding portion of the fiber may be configured to provide a second electro-magnetic radiation to the portion so as to modify at the property.

The apparatus can further include a dispersive arrangement configured to receive the first and second electromagnetic radiations. A wavelength of the first electro-magnetic radiation and/or the second electro-magnetic radiation can be a multiple of a wavelength of another one of the first electro-magnetic radiation or the second electro-magnetic radiation. The first electro-magnetic radiation and the second electro-magnetic radiation can at least partially overlap on the portion. The property may include blood. A wavelength of the second electro-magnetic radiation can overlaps with one or more certain wavelengths where an absorption of the radiation is effective for changing the property. Such certain wavelengths can include a multiple of about 532 nm.

According to yet another exemplary embodiment of the present invention, an apparatus can be provided for obtaining information for a structure. The apparatus can include a dispersive arrangement configured to receive a plurality of electro-magnetic radiations and forward a dispersed radiation of each of the electro-magnetic radiations to at least one portion of the structure and at least partially overlap the portion. One of the electro-magnetic radiations can have a wavelength in a first range, and another one of the electro-magnetic radiations may have a wavelength in a second range. Each of the first and second ranges can be at least one element that is different from another one of the second ranges. At least one first wavelength within one of the first and second ranges may be a multiple of at least one second wavelength within another one of the first and second ranges. The first wavelength can overlap with one or more certain wavelengths where an absorption of the radiation is effective for changing at least one property of the structure. Such certain wavelengths can include a multiple of about 532 nm.

These and other objects, features and advantages of the present invention will become apparent upon reading the following detailed description of embodiments of the present invention.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 8a is a schematic diagram of a measurement configuration, showing an exemplary embodiment of the SEE apparatus according to the present invention with respect to the tube and the flow direction;

FIG. 8b is a graph illustrating measured (e.g., solid curves) and calculated (e.g., dashed curves) cross-sectional flow velocities at the center of the tube shown in FIG. 8a;

FIG. 8c is a series of exemplary images of a two-dimensional measurement of the intralipid flow across the tube at different average flow velocities;

FIG. 8d is a set of combined flow and average reflectance images of, e.g., two 0.5 mm diameter tubes with similar and opposite flow velocities;

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention.

DETAILED DESCRIPTION OF EXEMPLARY EMBODIMENTS

Overview

An exemplary embodiment of the device/system/arrangement/apparatus according to the present invention can include, e.g., a 350-μm diameter SEE probe, constructed from a dual-clad fiber. According to this exemplary embodiment, a SEE imaging light can be transmitted through a central core, and an innermost cladding will guide high power 1064 nm light for vascular coagulation. In addition to providing simultaneous therapy, the exemplary system (and probe) can obtain color images using two separate wavelength bands, centered near 532 (VIS) and 1064 nm (NIR). Further, a spectral-domain heterodyne interferometry procedure and arrangement can be implemented to obtain three-dimensional images of chorionic plate topology and two-dimensional Doppler maps of blood flow. Provided below, exemplary results in accordance with exemplary embodiments of the present invention are described.

Summary of SEE and Exemplary Apparatus.

Figure 1:
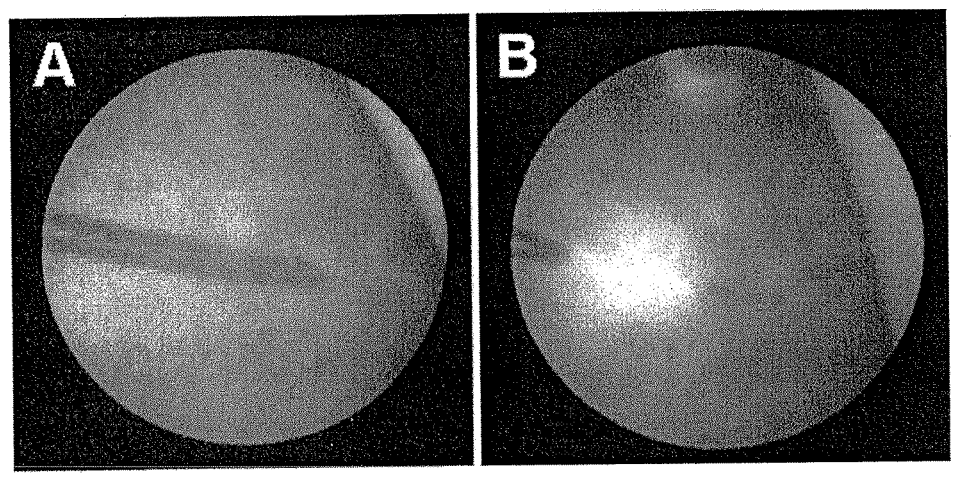
FIG. 1A is an exemplary fetoscopic image of an A-V anastomosis before a laser coagulation.
FIG. 1B is an exemplary fetoscopic image of the A-V anastomosis after the laser coagulation.
Figure 2:
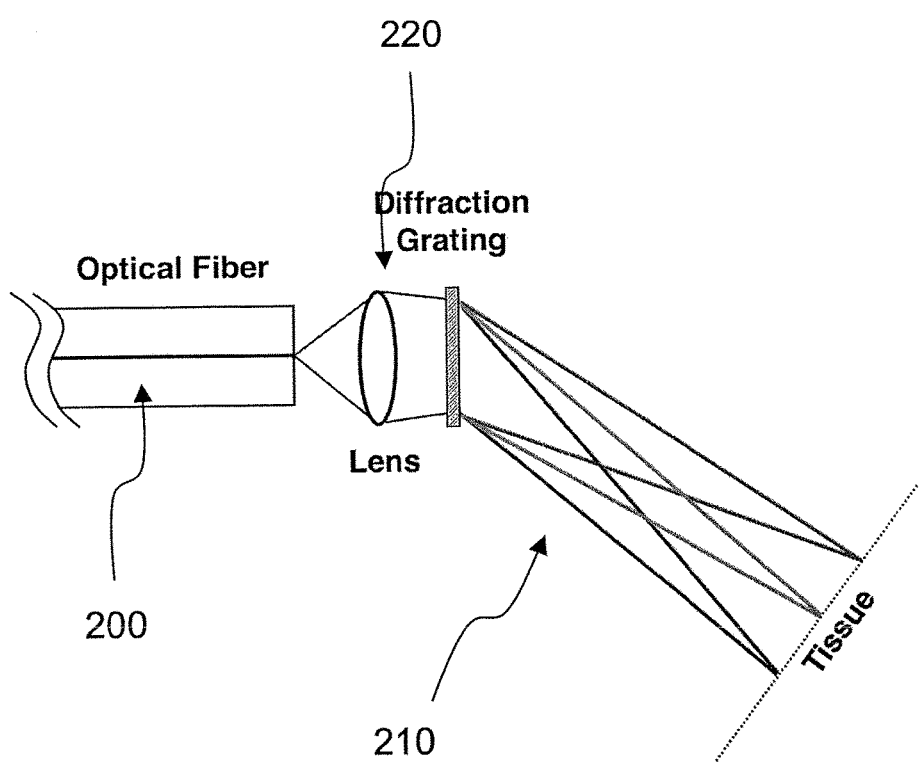
FIG. 2 is an operational diagram of an exemplary embodiment of an apparatus used in operation according to the present invention which implements the SEE procedure.
Figure 3:
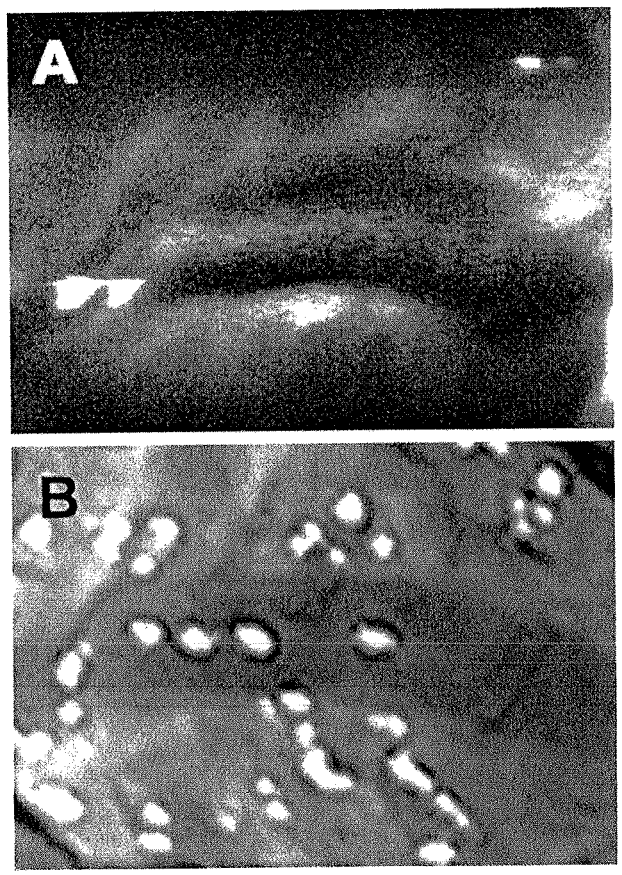
FIG. 3A is an exemplary image of a placenta obtained ex vivo with a first exemplary embodiment of the SEE apparatus according to the present invention.
FIG. 3B is an exemplary color (via gray scale) image corresponding to the exemplary image of FIG. 3A.

SEE was developed in 2001[32] when it was realized that the spectral encoding technology that has been developed for endoscopic confocal microscopy can provide more resolvable points for any given probe diameter than conventional fiber bundles.[36] An exemplary bench top system was constructed that utilized a 850 nm modelocked Ti:Al$_2$O$_3$ laser, a 1000 lines/mm transmission grating, and a CCD camera to obtain macroscopic images of excised specimens at video rates (30 frames per second).[32] Using a beam diameter of approximately 500 μm, the imaging of a placenta that was obtained postpartum was demonstrated (as shown in FIG. 3). The analysis indicated that the technology can be extended to increase the number of resolvable points by more than an order of magnitude.[32] Initial images compared favorably with those obtained by conventional fetoscopes with larger diameters.

Double-Clad Fiber SEE Apparatus.

Due to a coherent nature of light, SEE images obtained from a single mode fiber variably (generally) display speckle noise artifacts. To overcome these artifacts, an exemplary SEE imaging system can be provided that may illuminate the sample with single mode light through the core of a double-clad fiber and collected the remitted light through its innermost cladding.[37] Double-clad fibers can be obtained from commercially available sources. SEE images which cab be obtained with the double-clad fiber likely indicate a substantial reduction of speckle artifact, as well as an increased depth of field, both of which are highly desirable for endoscopy.[37] With an appropriate selection of the innermost cladding diameter, these advantages can be realized without significant loss in transverse resolution.[37]

Heterodyne Low-Coherence Interferometry for Three-Dimensional SEE Procedures.

It can be beneficial to facilitate optical low-coherence interferometry procedures for three-dimensional biological imaging.[38,39] Thus, a placement of the SEE apparatus/probe in the sample arm of an interferometer can provide three-dimensional information in addition to the standard two-dimensional view. For example, the exemplary SEE probe can be configured so that every resolvable point on the sample may be illuminated by light with a bandwidth sufficiently large to conduct low coherence interferometry at each spot. For small diameter probes, this exemplary configuration can be accomplished without the loss of a transverse resolution. Certain exemplary bench have been described for two different forms of a heterodyne interferometry, e.g., heterodyne speckle pattern subtraction[35] and time-domain low coherence interferometry.[34] Results obtained from these exemplary configurations demonstrates an ability of exemplary SEE procedures and apparatus to provide three-dimensional imaging at near real-time rates (e.g., 5 frames per second).[34] By leveraging the signal-to-noise ratio (SNR) advantages of spectral-domain low-coherence interferometry, it is possible to illustrate that three-dimensional images can be obtained at video rates.[33]

Exemplary 350-μm Diameter SEE Apparatus/Probe.

Figure 4:
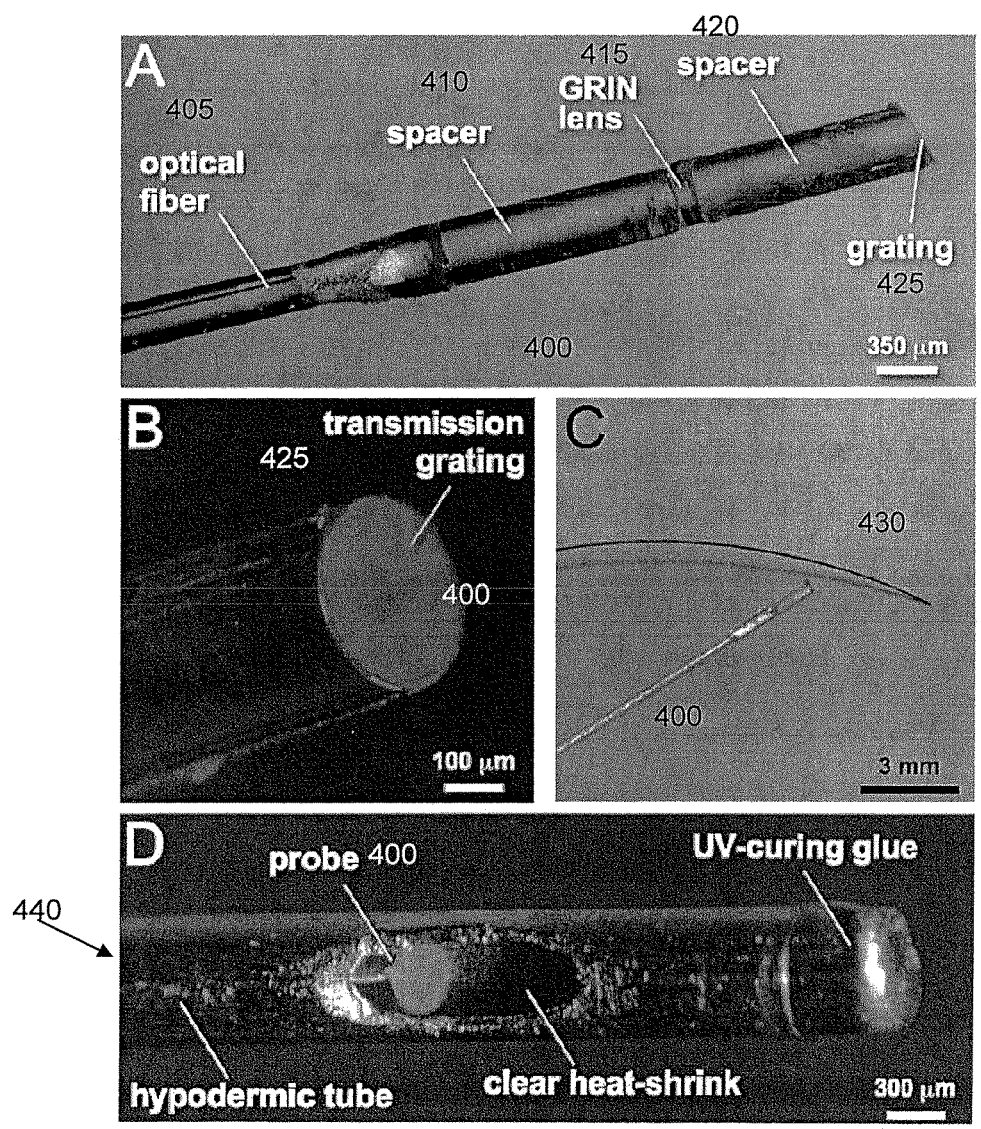
FIG. 4A is an exemplary illustration of a distal end of an exemplary embodiment of the SEE apparatus (e.g., probe) according to the present invention having, e.g., a 350 μm diameter.
FIG. 4B is an enlarged illustration of a diffraction grating provided at a tip of the exemplary apparatus shown in FIG. 4A.
FIG. 4C is the exemplary SEE apparatus that is illustrated next to a human hair (provided for size comparison)
FIG. 4D is a photograph of the SEE apparatus provided within, e.g., a 23-gauge stainless steel hypodermic tube which can be used for applications where the probe is delivered through a needle.

For example, to reduce the size of the exemplary SEE apparatus/probe, an exemplary diffraction grating can be incorporated directly onto the tip of an optical fiber. The exemplary grating can provide a high diffraction efficiency, may be robust to extremely high optical power densities, and likely be compatible with aqueous environments. Exemplary images of the exemplary embodiment of the SEE apparatus/probe 400 according to the present invention is shown in FIGS. 4A-4D.[33] For example, as shown in FIG. 4A, light from a single-mode fiber 405, expanded through a 1.8 mm long silica spacer 410, can be focused by a 350 μm diameter GRIN lens 415. Light from the lens 415 can then be diffracted by a 1000 lines/mm transmission grating 425 fabricated on a 1.5 mm long spacer 420 that can be polished at Littrow's angle of, e.g., about 19°. An expanded view of the diffraction grating 425 is shown in FIG. 4B. An exemplary maximum diameter of the exemplary apparatus/probe 400 can be about 350 μm; e.g., a size comparison between the exemplary apparatus/probe 400 and a human hair 430 is shown in FIG. 4C. Since the exemplary apparatus/probe 400 can be constructed from a single optical fiber, it may be very flexible, with a bending radius of approximately 2 mm, except within ~3.5 mm of the distal end.

SEE In Vivo Using the 350 μm Diameter Probe.

Figure 5:
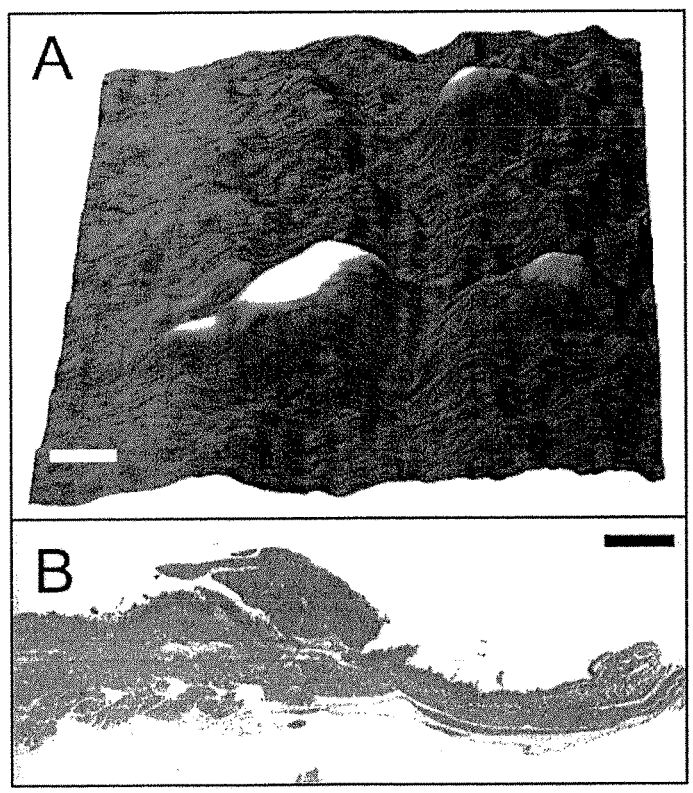
FIG. 5A is an exemplary SEE image of a metastatic ovarian cancer in vivo, where tumor nodules are shown on a parietal peritoneal wall of a mouse, according to an exemplary embodiment of the present invention.
FIG. 5B is a cross-sectional histological section from the corresponding area of FIG. 5A, showing tumor nodules (e.g., H&E stain; original magnification 40×), and scale bars representing 500 μm.

To demonstrate the exemplary SEE procedures and applications according to exemplary embodiments of the present invention in vivo, it is possible to image, e.g., metastatic ovarian tumors on the parietal peritoneum of a living mouse.[33] The exemplary 350 μm diameter SEE apparatus/probe 400 can be delivered into the abdominal cavity using a miniature laparoscopic through, e.g., a modified 23-gauge needle 440 (as shown in FIG. 4D). A small opening can be made in the needle wall, near its distal end, for the light to pass through. The opening can be sealed with a clear 6-μm thick layer of transparent plastic. A three-dimensional image of the parietal peritoneal wall, obtained with the SEE apparatus/probe in vivo, is shown in FIG. 5A. In this exemplary image, the two- and three-dimensional data sets can be combined to form a three-dimensional surface view of the tissue. A large, approximately 1 mm×1 mm×0.2 mm superficial tumor nodule can be seen near the center of the frame adjacent to two smaller 300×300×100 μm tumor nodules.

Differentiating Arteries from Veins.

In order for the user (e.g., surgeon) to identify A-V anastomoses, the exemplary apparatus (e.g., a microendoscope) can provide images with sufficient information to distinguish placental arteries from veins. In the placenta, arteries can be differentiated from veins by: i) color, ii) pulsatility/flow characteristics, and iii) a three-dimensional anatomic configuration, as arteries cross over veins on the chorionic plate.⁴⁰ By providing information on all three of these features, the exemplary embodiment of the SEE arrangement/device/system/apparatus/probe according to the present invention can facilitate the identification of more communicating vessels than the conventional two-dimensional procedure. As indicated herein, the exemplary SEE procedures and apparatus are capable of performing three-dimensional imaging. Provided below is a description of exemplary information in supporting the implementation and use of the exemplary embodiments of the procedures and apparatus for obtaining color and blood flow image data according to the present invention.

Exemplary Color Imaging Using 1064 and 532 nm Light.

Conventionally, SEE imaging has been monochromatic; broadband light centered at 850 nm has been used merely for encoding spatial information. The exemplary embodiments of SEE procedures and apparatus according to the present invention described herein can obtain color information by using two distinct wavelength bands, e.g., one centered near 1064 nm (NIR) and the other near 532 nm (VIS). This exemplary selection of wavelength regions can be appropriate since, the Nd:YAG therapy beam may overlap with the first and second order of the NIR and VIS imaging beams, respectively. In addition, the differential absorption of oxygenated and deoxygenated adult and fetal blood at VIS and NIR can be similar to that of the green and red wavelength bands used in standard RGB color imaging.⁴¹⁻⁴³

Figure 6:
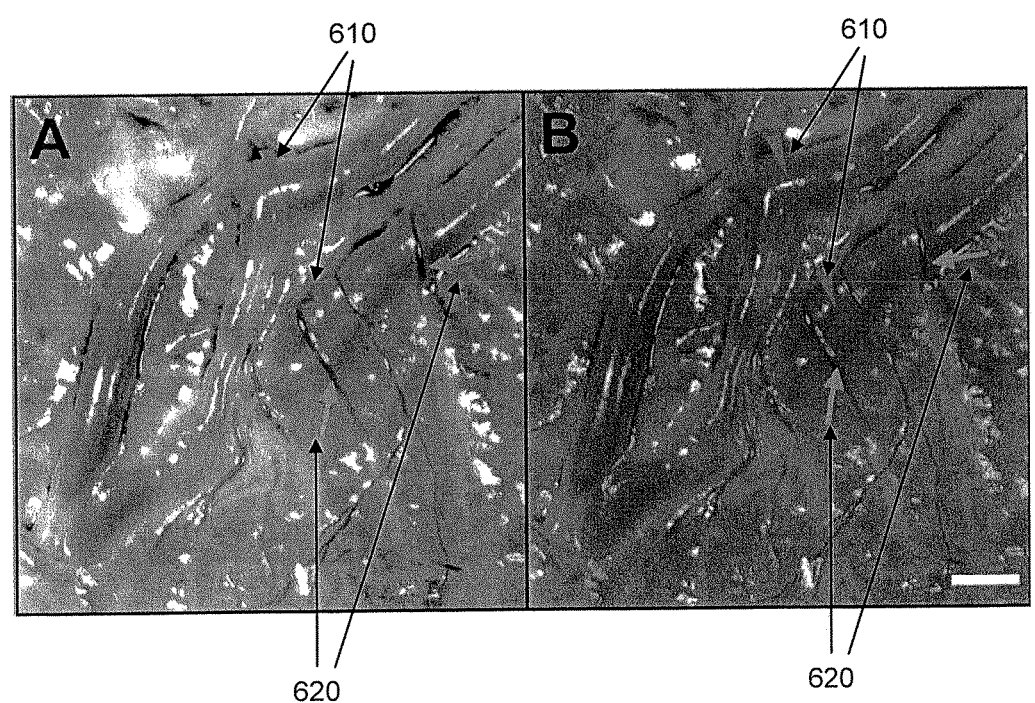
FIG. 6A is an exemplary VIS-NIR image of a human placenta, obtained postpartum, reconstructed using 532 nm and 1064 nm wavelengths, according to an exemplary embodiment of the present invention.
FIG. 6B is an exemplary RGB photograph associated with the image of FIG. 6A, with the bar being indicative of 5 mm.

To demonstrate the feasibility of artery and vein discrimination using the exemplary embodiments of the present invention, a placenta has been imaged, obtained immediately postpartum, with 1064±12 nm, 532±5 nm, and RGB light. A linear filter was first applied to the 1064 nm image data to remove noise. A VIS-NIR image (shown in FIG. 6A) was then generated by placing the 1064 nm image in the red channel and the 532 nm image in both the green and blue channels of a new 24-bit color image. No other manipulations other than contrast enhancement were made to the VIS-NIR image of FIG. 6A. The corresponding exemplary RGB image (in gray scale) is shown in FIG. 6B. By comparing the two images of FIGS. 6A and 6B, it is apparent that both have sufficient contrast to differentiate larger vessels, likely containing deoxygenated blood (shown as arrowheads 610) from smaller overlying vessels possibly containing oxygenated blood (shown as arrows 620). The smaller vessels are dark in the VIS-NIR image and darker in the image (red in a color image), which may be because of the absorption ratio of deoxygenated to oxygenated blood flips at the isosbestic point (~800 nm).⁴³ An understanding the color of blood vessels may be a complex task.⁴¹ Nevertheless, these exemplary results indicate that images obtained at such two wavelength regions can provide sufficient information to distinguish arteries from veins.

Doppler SEE Demonstration.

Figure 7:
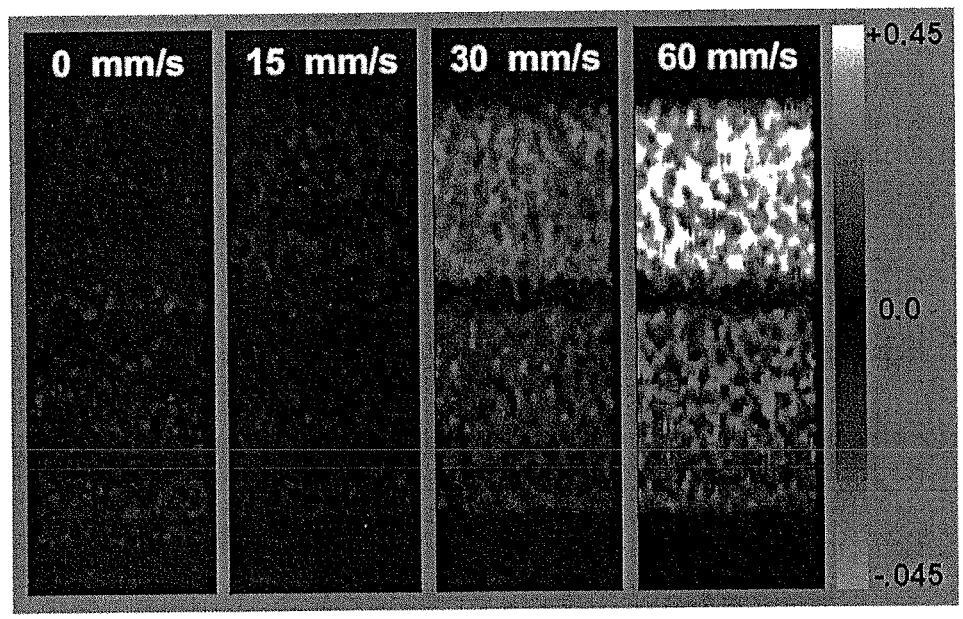
FIG. 7 is a set of exemplary two-dimensional Doppler SEE images of a dual-channel flowing Intralipid phantom obtained using an exemplary embodiment of the present invention.

In addition to obtaining three-dimensional information, exemplary SEE heterodyne interferometry procedures, conducted at each wavelength-encoded point on the sample, are capable of measuring the Doppler shift caused by blood flow. In order to demonstrate the feasibility of exemplary Doppler SEE procedures, a simple phantom has been produced, comprising a 1.0 mm diameter tube, looped back onto itself and affixed to a microscope slide. This phantom configuration can ensure that the exemplary SEE image may include two adjacent tubes with similar flow rates, with opposite flow directions. The tube was perfused with 10% Intralipid, which has a transport scattering coefficient similar to that of whole blood. Flow velocities were varied from about 0-60 mm/s, representing the approximate range of blood flow velocities that would be observed in a second trimester placenta and in TTTS.⁴⁴ Heterodyne spectral-domain SEE imaging of the phantom was conducted using our 350 μm diameter probe.³³ The spectral interferograms were processed using windowed short-time Fourier transforms to obtain local fringe magnitudes and phases.³³,³⁴ Doppler shifts at each point in the image were estimated by comparing the local phases of two adjacent spectrally-encoded lines. Two-dimensional flow maps (differential phase images) of the phantom (as shown in a set of exemplary images of FIG. 7) demonstrate that the exemplary heterodyne SEE procedures and apparatus may track the flow rate and direction throughout the entire velocity range. In particular, FIG. 7 shows flow directions (e.g., arrows) being along the horizontal dimension and flow velocities are shown at the top of each image (e.g., the exemplary images demonstrating a relationship between interferometric phase and flow velocity/direction, and differential phase magnitudes (a.u.) being plotted using a color Doppler lookup table depicted in the color bar).

Figure 8:
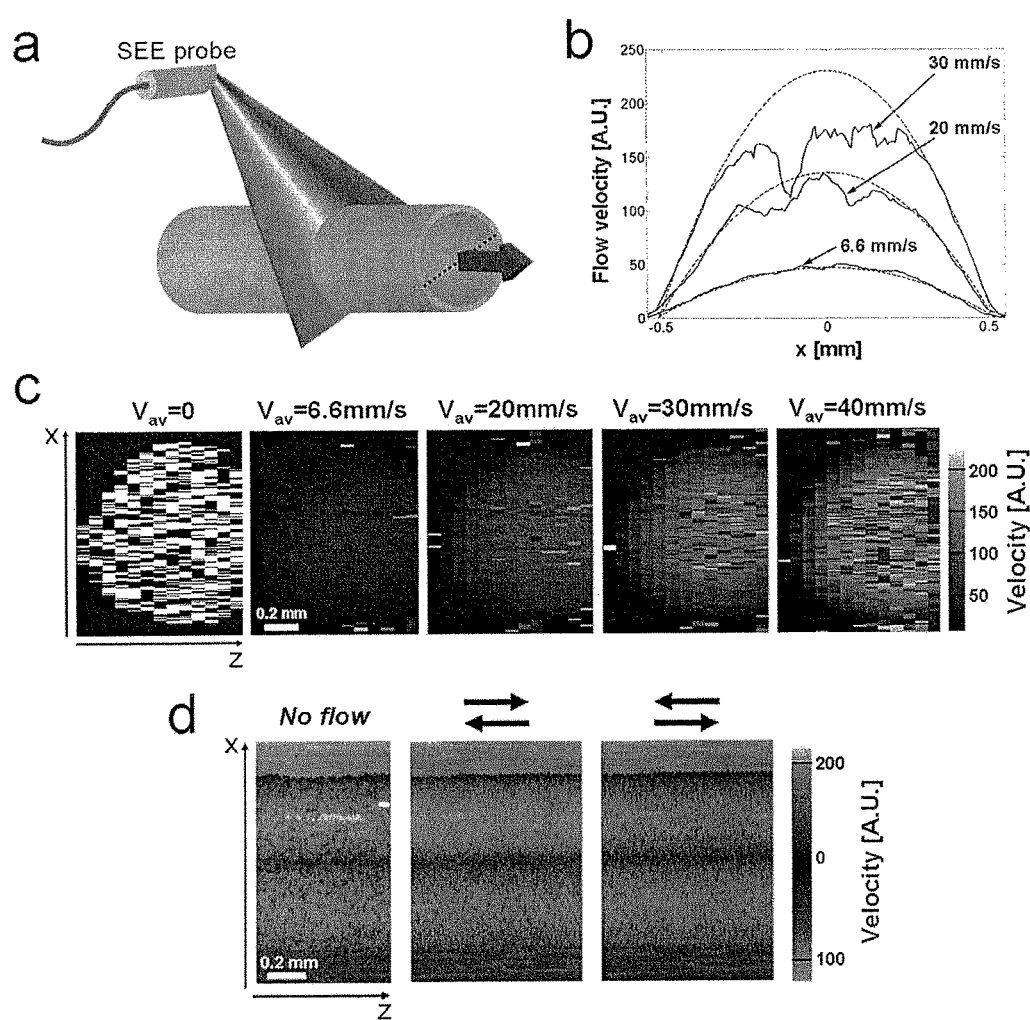

The exemplary embodiments of the SEE procedures and apparatus can also detect the flow at depth within scattering media and tissue. In order to demonstrate the ability of the exemplary SEE procedures and apparatus to image and measure flow, 1% intralipid may be circulated through a 1 mm diameter transparent tube. For example, the SEE beam can illuminate the tube as illustrated in FIG. 8a. Since the exemplary SEE procedures and apparatus can image through scattering medium [11], the x-z reflection data, when acquired as a function of time, can include information on the flow of scatterers throughout the entire cross section of the tube. The flow velocity and direction may be controlled by a peristaltic pump and its average value can be estimated by measuring the total volume that was flowing through the tube as a function of time. At average velocity of 6.6 mm/s and 20 mm/s flow velocity may show an inverted parabolic distribution, approaching zero at the tube walls. With the increase in pump speeds (average velocities of 30-40 mm/s), phase changes at the tube center became faster than the camera line rate (30 kHz), resulting with high error rates. An exemplary graph of a flow velocity profile at the center of the tube is shown in FIG. 8b for three different powers of the peristaltic pump. The solid curves represent the measured velocities calculated from the raw data according to Eq. 1.

$$v(x, z) = \frac{1}{k(x) \cdot \cos\theta} \cdot \frac{\partial \phi(k(x), z)}{\partial t}, \qquad (1)$$

where k(x) is the wave number and θ denotes the angle between the SEE beam propagation and the direction of sample motion.

The experimental data can be fitted with parabolic formulas:

$$v = -a \cdot x^2 + a \cdot R^2, \qquad (2)$$

where R=0.5 mm denotes the tube radius. The ratio between the average fitted velocities can be 1:2.6:4.4, which is in agreement with the measured average flow ratios of 1:3:4.5. An absolute value of the flow velocities may be difficult to obtain due to the relatively high uncertainty level in measuring the angle θ, which can be estimated to be in the range of about 80°≤θ<90°. A set of exemplary images of the two dimensional (x-z) distributions of flow velocity across the 1 mm diameter tube are shown in FIG. 8c for different pump powers. Without any pumping, FIG. 8c shows that the phase may fluctuate randomly and no flow was detected (e.g., left most image). At average velocity of 6.6 mm/s and 20 mm/s the flow velocity distributions can provide two-dimensional parabolic distributions with higher velocity in the center of the tube, approaching zero at the tube walls. Phase error at the tube's center may cause loss of data at higher flow velocities. Nevertheless, the flow profile may be estimated by fitting the parabolic curves to the areas closer to the tube walls, where flow is slower.

In addition to imaging flow speeds and direction, the exemplary embodiment of the SEE procedures and apparatus can additionally provide reflectance imaging of the tubes. To demonstrate simultaneous reflectance and flow imaging, two adjacent, 0.5 mm diameter transparent tubes, with similar but opposite flow directions, were imaged at 30 frames per second (30 kHz line rate). In the three exemplary images of in FIG. 8d, the intensity of each pixel represents the total reflectance, integrated over depth, and the color represents velocity, averaged over the tube's depth. With no pumping, the flow was likely random, resulting in purple hue in both tubes. With the average flow velocity of 5 mm/s in each tube, estimated by measuring the intralipid volume accumulated per 20 seconds, the different colors representing flows can be seen, with red [lighter] and blue [darker] hues corresponding to the flow in the right (left) direction.

Exemplary Design and Procedures

Exemplary Design

Placental laser coagulation therapy using 1064 nm light can be highly effective for interrupting twin-twin blood flow, but hampered by the large size of modern operative fetoscopes and their inability to image all communicating vessels. The exemplary embodiments of the procedures and apparatus according to the present invention can overcome these limitations by being significantly smaller and by providing more options for identifying A-V anastomoses. A first one of the exemplary objects indicated above can be focused on providing and testing an exemplary multifunctional SEE instrumentation of the exemplary SEE apparatus and procedure according to the present invention, combined with coincident high power laser irradiation. For a second one of the exemplary objects indicated above, 350 μm diameter exemplary SEE microendoscopes can be provided, integrated with the apparatus which can be implemented for the first one of the exemplary objects, and tested in phantoms and human tissue ex vivo. It is possible to use such exemplary procedures and arrangements, e.g., in a 10 pregnant ewes to demonstrate the feasibility of SEE-guided laser coagulation through an amniocentesis needle in vivo (see exemplary object 3).

Exemplary Procedures and Arrangements

Exemplary capabilities of the exemplary embodiment of the SEE-guided laser therapy apparatus according to the present invention can include, e.g., (a) high quality two-dimensional imaging, (b) three-dimensional, color, and Doppler imaging to identify A-V anastomoses, and (c) simultaneous laser therapy. In this Aim, we will construct a bench top exemplary SEE apparatus that can be used to design, implement, and validate different technical approaches for achieving these capabilities. The exemplary system can additionally be used to test and validate exemplary SEE probe configurations for the second exemplary object.

SEE Illumination.

Figure 9:
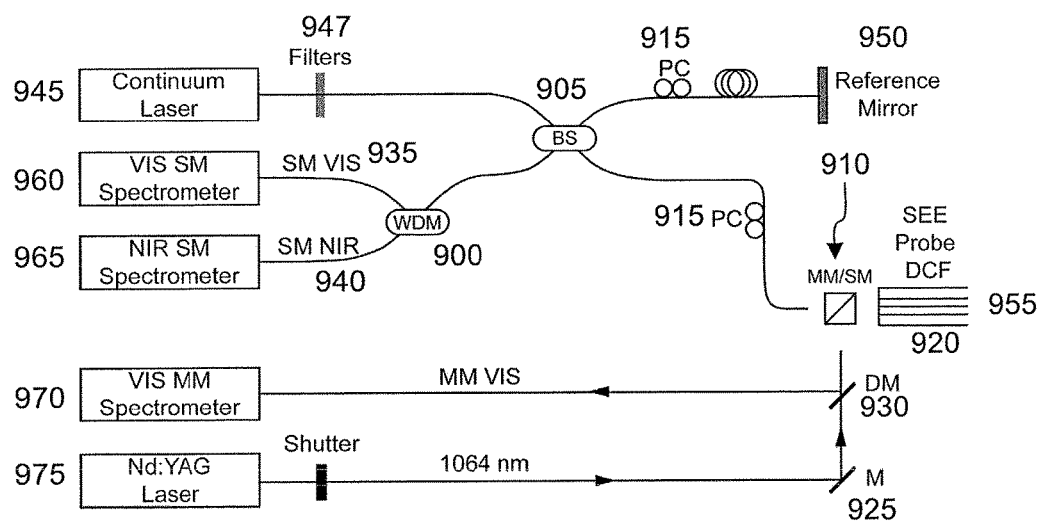
FIG. 9 is a schematic diagram of an exemplary embodiment of a SEE-guided laser therapy apparatus according to the present invention.

A schematic diagram of one exemplary embodiment of the SEE apparatus according to the present invention is shown in FIG. 9. The exemplary components of the exemplary system of FIG. 9 are as follows: WDM—wavelength division multiplexer 900, BS—beam splitter 905; MM—multimode, SM—single mode, SMF—single mode fiber, MM/SM—multimode/single mode splitter 910, PC—polarization controller 915, DCF—dual-clad fiber 920; M—mirror 925, DM—dichroic mirror 930, VIS—broadband light centered around 532 nm 935, and NIR—broadband light centered around 1064 nm 940. For example, light generated by a continuum source 945 can be filtered by a filter apparatus 947 to transmit broadband VIS (centered near 532 nm) and NIR (centered near 1064 nm) radiation. For three-dimensional and Doppler imaging, a small fraction of light can be directed towards a reference arm mirror 950. The remainder of the light can be transmitted through a single/multimode splitter 910, which can comprise a mirror with a central transparent opening that transmits single mode light and reflects multimode light. Following the transmission through the single/multimode splitter 910, the imaging light can be coupled to the core of the dual-clad fiber (DCF) of the SEE apparatus/probe 955.

Exemplary Bench Top Sample Arm Probe.

The exemplary sample arm probe can include the DCF, terminated by a lens and grating. In order to obtain a two-dimensional image, "slow axis" scanning can be performed using a galvanometer attached to the grating. This exemplary configuration can facilitate the testing of various approaches for color and Doppler imaging as well as probe components prior to the final microendoscope fabrication step. The exemplary SEE apparatus/probes can be incorporated into the exemplary system according to the present invention, e.g., for testing and other purposes.

Exemplary SEE Detection.

Following the reflection from the sample, light returned from the dual-clad fiber core and reference mirror can be recombined by the beam splitter 910 and separated into wavelength bands of the VIS 960 and NIR 965 using, e.g., a wavelength division multiplexer 900 or dichroic beam splitter. Each wavelength band can be detected by separate custom-built spectrometers, designed to measure spectral interferograms for 3D and Doppler flow map reconstructions. For a spectral detection, the VIS spectrometer 960 can utilize a high-speed Silicon linear CCD array while the NIR spectrometer 965 can employ an InGaAs linear array.[45,46] In order to obtain three-dimensional information, the spectral resolutions of the spectrometers can be approximately 5-10 times greater than the spectral resolution on the sample. Thus, linear array detectors can over-sample the spectral data so that approximately 5-10 pixels may be digitized for each resolvable point.[33]

Exemplary Image Reconstruction.

Two-dimensional, three-dimensional, Doppler, and color (VIS & NIR) SEE images can be obtained by computing windowed short-time Fourier transforms of the background-corrected spectral fringe data.[33,34] The two-dimensional image may be determined and/or generated based on, e.g., at least in part, the integrated power of the local Fourier spectra for each point. Color images can be generated by transforming the VIS and NIR SEE images into RGB space. While the VIS and NIR images can be co-registered and may have the same physical dimensions, the pixel density of the NIR image can be one-quarter that of the VIS image. The NIR image may therefore be interpolated prior to generation of the composite color image. Determining quantitative estimates of blood oxygenation content can also be analyzed using, e.g., two- and three-dimensional data sets at both wavelengths.[47-49]

The spectral power density of the continuum source can be, e.g., significantly higher than that of the source utilized in our preliminary studies. Thus, ample light can be provided to conduct shot-noise limited, depth resolved spectral-domain low coherence interferometry at each point in the image.[50] Reflectance as a function of depth within the tissue can be obtained from the magnitude of the local Fourier data. Phase dithering of the reference arm mirror may be used to eliminate or deduce depth degeneracy.[51,52] As a result, one line in the image can be generated from two linear array scans, where each scan may be acquired at a ~$\pi/2$ differential reference arm phase delay.[33] Doppler information can be obtained by determining the relative difference between Fourier domain phases at each location within tissue.[45,53,54]

Multimode Imaging.

Such exemplary embodiment of the system according to the present invention can also provides a speckle-reduction, which may be implemented by acquiring SEE images through the multi-mode inner cladding of the DCF.[37] To conduct multimode imaging, VIS light returned from the probe's innermost cladding may be reflected off the single/multimode splitter 910 and directed to another Silicon array spectrometer 970, which can be optimized for a multimode detection.

Exemplary Imaging System Performance.

For at least one of the exemplary embodiments of the small diameter probe/apparatus according to the present invention, the VIS wavelength band can provide 300 resolvable points across the image, resulting in a total two-dimensional pixel count of $300^2=90,000$, which is greater than that of commercially available fetoscopes with an order of magnitude larger diameter. At NIR wavelengths, the pixel count may be lower, approximating 22,500. Approximately 10 discrete axial locations can be obtained at each point, resulting in a total pixel count of $300\times300\times10\approx900,000$ in the volumetric images. For this example, axial resolutions for both the VIS and NIR channels can be ~280 μm. After resolving depth ambiguity, the total depth range can be approximately 3 mm for each wavelength region. If necessary for this application, greater depth ranges can be achieved by use of linear CCD's with higher pixel counts. The Atmel Silicon camera can sample 60,000 lines per second, whereas the InGaAs camera may generally operate at a line rate of 10 kHz. As a result, volumetric image data can be acquired at video rates for both VIS and NIR wavelengths.

Integrated Laser Therapy.

The exemplary embodiment of the SEE-guided laser therapy system, apparatus and procedure according to the present invention can integrate a therapeutic laser such as a Nd:YAG laser 975, thus meeting clinically-established specifications for the coagulation procedure. An operator-controlled pushbutton switch can activate a shutter that may remain open for 0.1 seconds every time the switch is activated.

Digitization, Storage, and Display.

Cameras can communicate to the host CPU via high-speed interfaces such as Camera Link. Assuming that exemplary highest 16-bit acquisition rates can be used for each camera, the total data rate may be approximately 310 MB/s, which is within the Camera Link DMA specification. For example, raw data can be stored in real time to a RAID array at rates such as 350 MB/s. A computing arrangement according to the can process the interferograms and display the exemplary resulting images. Since real-time complex FFT processing can be used to process and display all SEE images at video rate (e.g., 30 fps).

Exemplary Design Choices.

The exemplary embodiments of the apparatus, system and components according to the present invention can include various designs.

a) Exemplary Technology for Differentiating Arteries and Veins.

During fetoscopy, fetal surgeons currently use three cues to differentiate placental arteries from veins: color, pulsatility, and three-dimensional anatomical structure.[40] The exemplary embodiment of the SEE system and apparatus according to the present invention is capable of measuring all three of these features, with higher resolution and in a quantitative manner that should be superior to qualitative interpretation of conventional two-dimensional fetoscopic images. Exemplary SEE Doppler flow imaging capabilities can be included in the exemplary SEE system to improve the surgeon's ability to see A-V anastomoses. Exemplary advantages of an exemplary multifaceted procedure and apparatus for identifying communicating vessels at this development phase can include redundancy; if one approach becomes intractable.

b) Wavelength Selection.

An exemplary selection of VIS (e.g., centered around 532 nm) and NIR (centered around 1064 nm) wavelength regions is based on a preference to minimize the diameter of the SEE probe and the use of standard, high power 1064 nm light for placental vascular coagulation. It is possible to use other exemplary wavelengths where the fundamental can also effect a substantial vascular coagulation. Alternatively, a probe with several fibers may be provided. In such case, the first fiber can deliver high-power 1064 nm light and the other fibers may be used for SEE imaging at wavelengths other than VIS and NIR, such as red (e.g., 600-700 nm), green (e.g., 500-600 nm), and blue (e.g., 400-500 nm). Even with a four-fiber approach, the resultant exemplary SEE-guided laser therapy probe/apparatus can be significantly smaller than operative fetoscopes.

c) Heterodyne Interferometric Systems.

Heterodyne interferometry can be conducted for both VIS and NIR wavelength regions, since VIS imaging may have the highest spatial resolution and NIR imaging can penetrate deeper into tissue owing to decreased scattering. It is also possible that only one of these exemplary wavelength bands can be used to provide three-dimensional structural and flow cues required for optimal identification of A-V anastomoses. In such case, it is possible to eliminate one of the spectrometers from the interferometer and use these components for another multimode detection channel.

d) Multimode Imaging.

According to the exemplary embodiment of the present invention, the VIS band can be used for a multimode detection, due to the higher number of resolvable points attained by SEE at these wavelengths. It is possible that further multimode NIR information may be provided for high-quality two-dimensional imaging. In this case, it is possible to partition the InGaAs linear array so that approximately 100 pixels can be utilized for multimode detection while the remaining pixels may be reserved for heterodyne detection.

Exemplary Procedures

Herein below is a description of exemplary procedures and tests that can be utilized to construct and verify the performance of the exemplary embodiment of the SEE-laser coagulation therapy system and apparatus according to the present invention:

a. SEE Light Source.

Free-space and DCF-coupled power from the fiber-pumped continuum source can be measured for each bandwidth region. Different combinations of filters, gratings, and fiber optics may be used to shape the spectrum in each wavelength band to ensure that they are sufficiently uniform for efficient image reconstruction. Spectral stability can also be measured. If significant spectral variation is present, it is possible to use either a separate photodiode or an additional spectrometer to collect background spectra for real time correction of the spectrometer data.

b. Fiber Optics.

Due to stability and convenience, fiber in the optical train can be desirable. However, it may be unlikely that single-mode fibers and the core of the DCF may be single mode for both wavelength regions. Furthermore, reference and sample arm polarization balancing may be difficult to achieve in the VIS and NIR wavelengths simultaneously. Thus, it is possible to use various fiber optic and free space components to identify the most stable, compact system that produces high quality images.

c. Spectrometer Subsystems.

Spectrometers can be designed using a variety of lenses, transmission gratings, and reflection gratings may be tested for maximum throughput and spectral resolution. Spectrometer throughput can be determined by comparing power at the input and at the array detector. Spectral resolution may be obtained at the ends and middle of the two spectral ranges for each interferometer by measuring the full-width-half-maximum of coherent narrow band laser light. Heterodyne SNR can be determined for each spectrometer by placing an attenuator and mirror in the sample arm, measuring the demodulated signal, and the noise with the sample arm blocked.

d. Image Quality.

Imaging performance can be assessed using a bench top sample arm probe that simulates the optical characteristics of the small diameter exemplary SEE probe (see exemplary object 2). Images of resolution charts and phantoms can be quantitatively analyzed to measure transverse and axial resolutions. Measurements may be compared to computer models and analytic simulation results. Image quality metrics may serve as feedback information for exemplary embodiments of the system according to the present invention.

e. Color Imaging.

A variety of techniques can be reviewed for quantitative and qualitative analysis of color from the VIS and NIR images. Vessel phantoms containing both scattering media and human blood with varying oxygen content can be constructed. Monte Carlo modeling can be performed to determine the relationships between diffusely and singly scattered light from phantoms with different degrees of oxygenation. Based on the phantom measurement and modeling results, exemplary procedures can be implemented for a vessel characterization that can combine two- and three-dimensional information in the VIS and NIR wavelength regions. Quantitative exemplary procedures for estimating blood oxygenation content can be utilized that may use the differential oxy- and deoxy-hemoglobin absorption spectra. Exemplary procedures for reconstituting images that approximate the conventional RGB color view may also be developed. In short, digital photographs and SEE images of phantoms and human placentas (see below) can be acquired and their color space representations may be compared. Relationships between features extracted from the two color spaces may be determined and multivariate data analysis and error function minimization will find optimal mappings from VIS-NIR to RGB color spaces.[55,56]

Performance of the exemplary procedures can be evaluated by testing them on blood phantoms and human placentas with arteries and veins that have been filled with heparinized deoxygenated and oxygenated blood, respectively.[57] Imaging can be conducted through saline. Observers, blinded to blood oxygen content and vessel type can discriminate artery from vein in both SEE color images and corresponding RGB color fetoscopy images. Sensitivity and specificity for color SEE and standard fetoscopy may be determined using knowledge of vessel type as the gold standard. Sensitivities and specificities for the two modalities can be compared using McNemar's test. Quantitative SEE assessment of oxygen content can be compared with known oxygen content by linear regression. If these two wavelength regions are insufficient for meeting our milestones, alternative wavelength bands may be provided.

f. Flow Imaging.

Self-referencing exemplary procedures for extracting the phase from the exemplary heterodyne VIS and NIR SEE systems and apparatus can be provided and tested in moving phantoms with known velocity. Flow rates may approximate that in the normal placenta and TTTS cases (e.g., 0-60 mm/s).[44] Flow velocity, velocity variance, power Doppler, and Doppler spectral images can be determined from the phase information.[58] Since the exemplary probe/apparatus beam may not typically be perpendicular to the chorionic plate, angular differences between the optical axis and flow direction would likely not greatly affect relative measurements of flow. It is possible to validate the expected $\cos(\theta)$ relationship and determine its effect on flow imaging maps constructed from phantoms. Phantoms and human placentas can be perfused with heparinized blood through the umbilical vein in a pulsatile manner that simulates maternal-fetal circulation.[57] Time-resolved and time-averaged SEE cross-sectional measurements of flow velocity and average power Doppler signal may be compared with Doppler ultrasound using paired t-tests.

g. Artery Vs. Vein Differentiation.

As described above, human placentas, obtained postpartum can be perfused with pulsatile blood. In a separate set of placentas, arteries and veins can be then imaged through saline by SEE and state-of-the-art fetoscope instrumentation. The trained fetal surgeon, blinded to the vessel type, can identify arteries and veins using both technologies. Sensitivity and specificity of the two technologies for categorizing artery versus vein can be determined. Sensitivities and specificities of the two exemplary embodiments may be compared using McNemar's test. Histology can be used as a standard.

h. Nd:YAG Laser Power and Coupling.

The power of the Nd:YAG laser can be measured before and after propagation through the prototype system optics. Optics for coupling into the DCF may be designed using computer modeling. Fiber coupling efficiency can be measured. All optics including the DCF, multimode splitter, fiber coupler, and bench top probe lens/grating pairs can be exposed to continuous and 0.1 s pulsed high power 1064 nm light. The powers preferred (e.g., 40-100 W) would likely not damage the gratings, since in the unlikely worst case scenario, the estimated maximum energy density may be four orders of magnitude lower than the lower bound of their exposure limit.[59] These and other exemplary components can be evaluated for signs of laser-associated damage and other more preferable components can be provided if damage occurs.

i. Nd:YAG Placental Vascular Photocoagulation Experiments.

Vascular coagulation therapy can be conducted in free space and through saline using the aforementioned Nd:YAG laser, coupled through the system into the DCF. Human placentas, obtained postpartum may be perfused with human blood. Nd:YAG laser pulses (0.1 sec) can be transmitted through the bench top sample arm probe and aimed at human placental arteries and veins. The number of pulses may be varied for different vessel diameters and types to optimize exposure parameters. Vascular coagulation tests can also be conducted on adjacent locations with standard Nd:YAG instrumentation from the fetal surgery unit. Spatial extent of vascular coagulation can be evaluated using quantitative histomorphology and compared between the two surgical devices using paired t-tests.

j. System Integration.

The exemplary system according to the present invention can be incorporated, e.g., into a portable cart for ease of use in the surgical suite. Software can be provided to store the data in real-time to the RAID, and to generate and display the exemplary two-dimensional, three-dimensional, color, and Doppler SEE images.

Exemplary Testing

In order to conform the operation of the exemplary embodiment of the SEE system and apparatus according to the present invention for a microendoscopic laser vessel coagulation, the following Objective Performance Targets (OPT) can be reviewed:

a) Continuum source spectral variation: ≤10%. In order to ensure adequate image quality, and good spectral stability, spectral variation can be confirmed by measuring the temporal variance of the corrected spectrum in exemplary two wavelength bands described herein.

b) Sustained display rate: ≥30 fps. Video rate imaging may be preferable for endoscopically-guided intervention. Display rate can be measured for the exemplary two-dimensional SEE images.

c) Sustained data storage rate: ≥150 MB/s. The raw data from the spectrometers can be digitally stored in real-time. Such data storage rate would likely be sufficient to recover all images at video rate.

d) Spectrometer spectral resolution ≤0.1 nm. This spectral resolution can provide up to 4 mm depth range for our heterodyne SEE low-coherence interferometry systems, which is adequate for determining placental vascular three-dimensional anatomy. This exemplary metric can be determined as described herein above.

e) Heterodyne SNR: ≥105 dB. This OPT can facilitate allow imaging at up to 500 μm in tissue at the VIS wavelength region and approximately 3 mm at NIR. These penetration depths can be sufficient to image through the artery and vein walls to measure Doppler signal from flowing blood. This exemplary metric can be determined as described herein above.

f) Nd:YAG coupling efficiency: ≥50%. Based on data from current Nd:YAG systems, 25 W can be sufficient to effect satisfactory placental vessel coagulation.[2] Assuming 50% Nd:YAG throughput for the innermost cladding of the SEE probe, a coupling efficiency of >50% may exceed this exemplary threshold value on the placenta. Laser power before and after the DCF can be used to evaluate this metric.

g) Transverse resolution: factor of 2 deviation from theory. Exemplary transverse resolutions of the exemplary embodiment of the SEE systems according to the present invention can depend on the grating and lenses used in our bench top probe. The exemplary transverse resolution can match theoretical resolutions within a factor of two. Transverse resolutions may be measured by SEE imaging of resolution standards.

h) Number of spectrally resolvable points: 200 at VIS, 100 at NIR. Such OPT can be the number of resolvable points in the best commercially available fetoscope. Number of resolvable points may be determined by dividing the field of view by the measured transverse spatial resolutions.

i) Speckle reduction for multimode system: ≥10 dB increase in SNR. Review of dual-clad SEE demonstrates that a factor 10 increase in SNR can provide natural appearing images with a large depth of field. SNR can be measured on single- and multimode VIS images of human placentas, obtained postpartum.

j) Nd:YAG vascular photocoagulation: Equivalent to or better than standard of care. Exemplary metric can be determined as described herein above.

k) Color imaging: Equivalent to or better than fetoscopy. Exemplary metric can be determined as described herein above.

l) Flow imaging: R≥0.6. Exemplary flow velocities measured by phase-SEE and a flowmeter can be obtained over the velocity range of about 0-60 mm/s[44] and compared using linear regression. A Pearson's correlation coefficient of R>0.6 can be considered a good or substantial agreement between the two measurements.

m) Vessel identification: Equivalent to or better than fetoscopy. Exemplary metric can be determined as described herein above.

Further, since exemplary probe/apparatus diameter can be proportional to fetal complication rate, the preferable instrumentation may have a small or minimal size. It is possible to provide an exemplary small (i.e. 350 μm) diameter guided laser therapy probe/apparatus that may be compatible with the advanced capabilities described above with respect to exemplary object 1, and that can be also an order of magnitude smaller than operative fetoscopes in clinical use. Thus, it is possible to administer this exemplary device/probe/apparatus into the amniotic cavity through a small-diameter amniocentesis needle, resulting in a 10-fold reduction in iPPROM and IUFD, compared with current operative fetoscopy.

SEE Microendoscope Description

Figure 10:
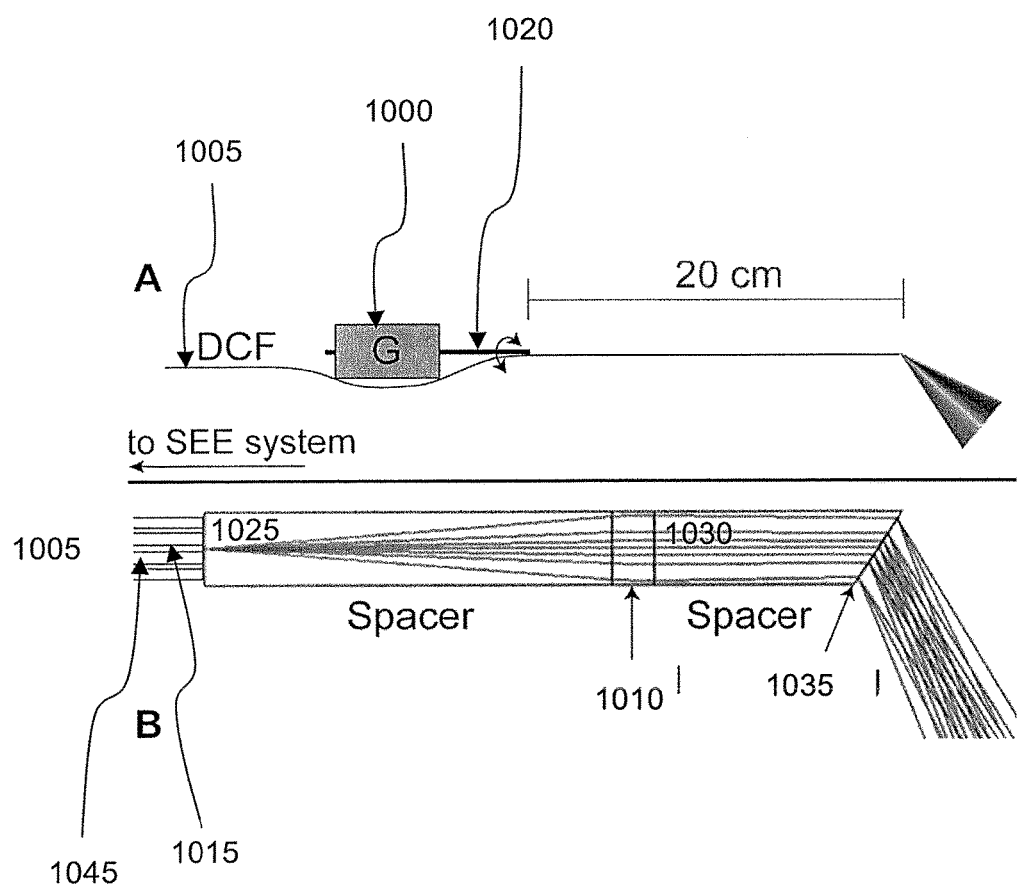
FIG. 10A is a schematic diagram of another exemplary embodiment of the SEE arrangement (e.g., probe) according to the present invention.
FIG. 10B is an exploded view of optics at a distal end of the exemplary arrangement of FIG. 10A.

The exemplary embodiment of the SEE microendoscope arrangement and apparatus according to the present invention shown in FIGS. 10A and 10B has some similarities with the 350 μm diameter miniature endoscope previously described for use in vivo.[33,37] In FIGS. 10A and 10B, the components are labeled as follows: G—galvanometer 1000, DCF—dual-clad fiber 1005, and GRIN—gradient index lens 1010. To summarize, broadband VIS and NIR light can be coupled into the core of the DCF 1015 for effectuating SEE imaging. The proximal end of the fiber may be affixed to a galvanometer shaft 1020. When the shaft rotates, the fiber 1005 can rotate with it throughout its length, enabling "slow axis" scanning of the second dimension of the image.[33] The DCF 1005 can be fusion spliced or affixed to a silica spacer 1025, gradient index lens 1010, and another spacer 1030 that may be polished at Littrow's angle of the diffraction grating. The replicated holographic transmission grating 1035 may be stamped onto a hard epoxy coating on the exposed face of the second spacer. An outer housing of the probe can be a 22-gauge amniocentesis needle, e.g., similar to that used in the exemplary microlaparoscopic procedure provided on living mice (see FIG. 4D).[33] Both the core 1015 and innermost cladding 1045 can collect light reflected from the subject. Core light may be directed to the VIS and NIR interferometric spectrometers. For example, innermost cladding light can be detected by the multimode spectrometer (as shown in FIG. 9) to obtain an image with minimal speckle noise and an increased depth of field. High-power laser therapy light may be delivered through the innermost cladding of the DCF 1045 to the tissue for vessel coagulation.

Exemplary Probe Optics.

The exemplary configuration of the probe/apparatus optics according to the present invention can be based on, e.g., (a) field of view and working distance specifications of state-of-the-art fetoscopes for safe placental laser vessel coagulation procedures,[3,40] (b) viewing angle considerations to provide optimal surgical guidance, (c) appropriate wavelengths for distinguishing arteries from veins, and (d) the constraints placed on the microendoscope by a selection of an exemplary coagulation laser wavelength. There may be many degrees of freedom in the optical design parameters, including center wavelength and bandwidth of the imaging wavelength regions, grating groove density, lens focal length, and DCF core and innermost cladding numerical apertures.

TABLE 1

| Specification | State-of-the-art fetoscope | SEE-microendoscope |
| --- | --- | --- |
| Field of view | 3 cm | 1-3 cm* |
| Depth of focus | 5 cm | 5 cm |
| View angle | 0° | 70° |
| Diameter (area)† | 2.0 mm (8.5 mm$^2$) | 350 μm (0.4 mm$^2$) |
| Max. res. points | 50,000 | 90,000 |
| Tx spot diameter | 1 mm | 1 mm |

Table 1 summarizes the optical parameters and performance characteristics of one design that balances the desired requirements of an operative fetoscope, while still maintaining good imaging performance. In this table, an exemplary specifications of an exemplary SEE therapy probe/apparatus and fetoscope are provided.[1-3] This exemplary embodiment of the probe/apparatus can provide for 1 cm FOV along the spectrally-encoded axis and 3 cm along the slow-axis of scanning. †Cross-sectional area may be determined from diameters of 3.3 mm trocar required for the Storz operative fetoscope[3] and a 22-gauge needle for the SEE-microendoscope.

Figure 11:
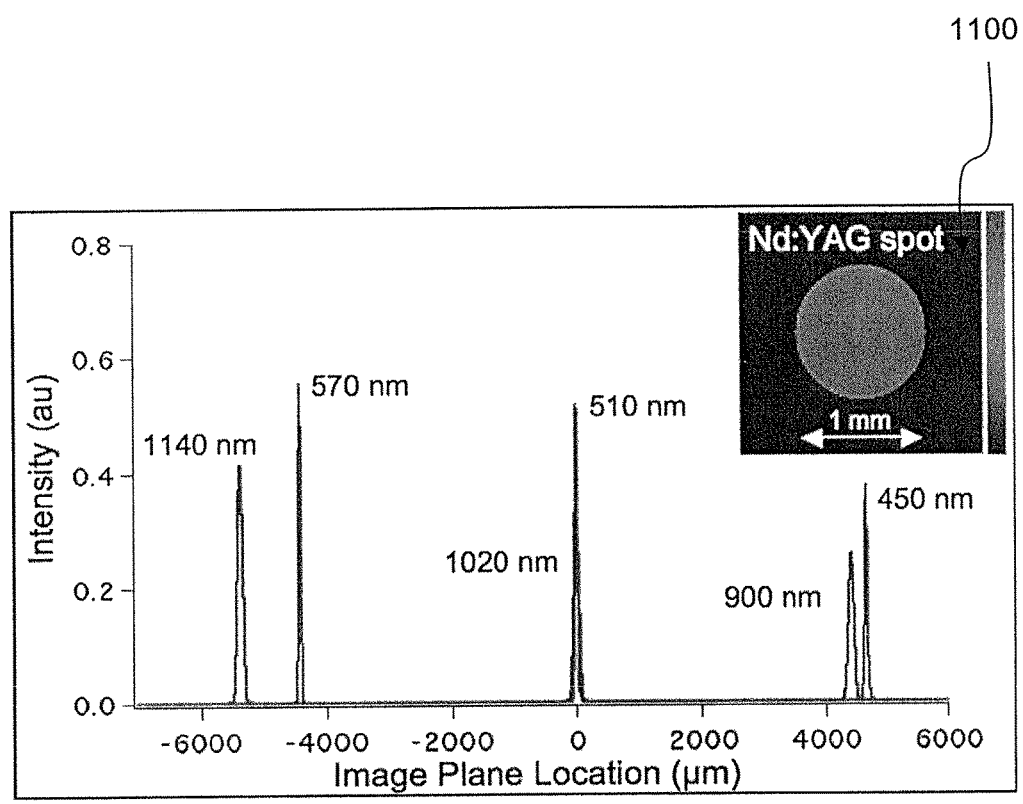
FIG. 11 is an exemplary graph of transverse PSFs for visible (e.g., green, m=2) and near-infra red (e.g., red, m=1) diffracted orders at the image plane (3 cm from probe tip).

This exemplary configuration and the entire parameter space can be analyzed to identify the optimal or preferable configuration for this exemplary application. For example, with the exception of viewing angle, the field of view, and diameter, this exemplary SEE microendoscope/apparatus may have comparable design specifications to the conventional operative fetoscope. However, an angled view can be easier to use than the forward-looking view of prior technology.[40] Maximizing the field of view based on the exemplary embodiment of the present invention is one of the objects of the present invention. For this exemplary configuration, the spectral bandwidth may be maximized in order to increase the field of view. Since, it may be less preferable for the long-wavelength portion of the NIR beam to overlap with wavelengths where water absorption is strong, it is possible to blue-shift the center wavelength by a minor amount (~15%). As a result, the centroid of the therapy beam can be slightly shifted from the center of the image. A computer simulation may be conducted to validate such exemplary configuration, possibly demonstrating near diffraction-limited performance at both imaging wavelengths and an appropriate beam profile for laser therapy (see graph of FIG. 11). For example, an inset of the graph of FIG. 11 shows the beam profile 1100 for the Nd:YAG laser spot. Simulation parameters: DCF innermost cladding can be as follows: 100 μm; DCF NA: 0.12; GRIN polished to 0.20 mm thickness; grating groove density: 1500 lines/mm; Littrow's angle (saline) 34°.

Further Exemplary Procedures

Described below are further exemplary embodiments of procedures and tests according to the present invention that can be utilized to construct and verify the performance of the SEE-laser therapy microendoscope/apparatus:

a) Optical design. Computer modeling can be conducted to analyze the optical design parameter space. DCF's with a variety of core and innermost cladding diameters, and numerical apertures may be designed. High groove density transmission gratings can be designed for both air and saline immersion that can provide >75% diffraction efficiency for both wavelength regions.[60] A variety of different possibilities for increasing field of view along the spectrally-encoded axis may be reviewed, including using a miniature fish-eye lens, placing the grating prior to the lens, and increasing the spectral bandwidths/grating groove densities further.

b) Optical fabrication. DCF's can be drawn, characterized and tested for imaging. Silica spacers may be cut to the appropriate length and angle polished to minimize backreflections (Spacer 1) and to provide Littrow's angle (Spacer 2). Distal silica spacers may be assembled in a custom mount and provided for transmission grating deposition. Exemplary components may then be tested individually for their optical characteristics, including the existence of visible defects, grating diffraction efficiency, backreflections, and aberrations. Individual components can be assembled using optical adhesives that can withstand high power 1064 nm exposure.

c) Amniocentesis needle. The 22-gauge amniocentesis needle can serve two exemplary purposes: i) it may house the DCF and optics to enable "slow axis" scanning and ii) it can serve as the miniature trocar for inserting the imaging probe/apparatus into the amniotic cavity. The tip of the needle may be open or closed by epoxy. When the tip is open, the optics can emerge from the tip for scanning externally to the needle. Exemplary advantages of this exemplary approach are that saline can be perfused through the needle to clear the field of view and lack of aberrations. However, in this case, the probe/apparatus optics may not be protected. The optics can generally be protected when the tip is closed, but a transparent window is then used in the needle (see FIG. 4D), which may cause aberrations. Both of these exemplary configurations can be tested on resolution standards and saline-filled phantoms to determine the appropriate choice for this exemplary application.

d) Mechanics. Fiber rotation can convey mechanical motion from the proximal to distal ends of the exemplary SEE probe/apparatus.[33] Thus, the exemplary embodiment of the probe according to the present invention can be two times longer, and the motion transduction can be confirmed for a variety of fiber buffer materials.

e) Testing. Once the exemplary probes/apparatus are fabricated, it is possible to test each probe for insertion loss and backreflections within each wavelength region. Transverse resolution, depth of focus, field of view, and beam quality at the focus can be determined by use of a slit-scanning beam profiler and exemplary SEE imaging of resolution charts.

f) Validation. Exemplary testing procedures described above with the integrated exemplary SEE system, apparatus and probe can be used herein.

In order to demonstrate suitability of the bench top SEE probe/apparatus for microendoscopic laser vessel coagulation the following Objective Performance Targets (OPT) can be, e.g.:

a) Single-pass core insertion loss: ≤5 dB. Given the power spectral density of our continuum source, high-quality imaging can be conducted with a single pass loss less than or equal to this OPT.

b) Imaging backreflections: ≤30 dB. The exemplary upper bound on probe back-reflections can be preferable for high-quality imaging that may be measured by comparing returned signal powers with and without a mirror at the image plane of the exemplary probe/apparatus.

c) Field of view at image plane: ≥1 cm. This OPT can be comparable to that of commercially available fetoscopes and may be measured by imaging resolution standards at the image plane.

d) Depth of focus: ≥4.0 cm. This OPT can be comparable to that of commercially available fetoscopes and may be measured by imaging resolution standards below the image plane.

e) Imaging rate: ≥30 Hz. Video rate imaging can be preferable for endoscopically-guided intervention, and the display rate may be determined for the exemplary two-dimensional SEE images.

Nd:YAG inner cladding transmitted power: ≥25 W. Laser vessel coagulation can be effectively conducted with this OPT.[2]

g) Nd:YAG induced probe damage: None. This OPT can be evaluated by conducting SEE imaging after continuous and repeated exposure of, e.g., high power 1064 nm light.

In another exemplary object of the present invention is to test the SEE visualization and therapy system developed as described herein above. Image-guided therapy can be conducted, e.g., in 10 pregnant ewes using the exemplary device through an amniocentesis needle and conventional operative fetoscopy equipment. Safety of the exemplary device/apparatus can be evaluated by comparing damage that occurs at the maternal incision and uterine entry sites. Efficacy may be measured by comparing a) the accuracy of each exemplary technique for differentiating artery from vein, and b) diagnoses obtained at sites of laser photocoagulation. Histopathology can be the standard. Following completion of this exemplary procedure, data can be provided in support of this procedure for treatment of TTTS.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with any OCT system, OFDI system, spectral domain OCT (SD-OCT) system or other imaging systems, and for example with those described in International Patent Application PCT/US2004/029148, filed Sep. 8, 2004, U.S. patent application Ser. No. 11/266,779, filed Nov. 2, 2005, and U.S. patent application Ser. No. 10/501,276, filed Jul. 9, 2004, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

REFERENCES

1. Bussey J G, Luks F, Carr S R, Plevyak M and Tracy T F, Jr. Minimal-access fetal surgery for twin-to-twin transfusion syndrome. Surg Endosc 2004; 18:83-6.
2. Lewi L, Van Schoubroeck D, Gratacos E, Witters I, Timmerman D and Deprest J. Monochorionic diamniotic twins: complications and management options. Curr Opin Obstet Gynecol 2003; 15:177-94.
3. Senat M V, Deprest J, Boulvain M, Paupe A, Winer N and Ville Y. Endoscopic laser surgery versus serial amnioreduction for severe twin-to-twin transfusion syndrome. N Engl J Med 2004; 351:136-44.
4. Deprest J A and Gratacos E. Obstetrical endoscopy. Curr Opin Obstet Gynecol 1999; 11:195-203.
5. Deprest J A, Lerut T E and Vandenberghe K. Operative fetoscopy: new perspective in fetal therapy? Prenat Diagn 1997; 17:1247-60.
6. Danzer E, Sydorak R M, Harrison M R and Albanese C T. Minimal access fetal surgery. Eur J Obstet Gynecol Reprod Biol 2003; 108:3-13.
7. Huber A, Diehl W, Bregenzer T, Hackeloer B J and Hecher K. Stage-related outcome in twin-twin transfusion syndrome treated by fetoscopic laser coagulation. Obstet Gynecol 2006; 108:333-7.
8. Lau T K, Leung T Y, Fung T Y and Leung T N. Treatment of twin-twin transfusion syndrome by fetoscopic laser photocoagulation. Chin Med J (Engl) 2004; 117:1431-4.
9. Gardiner H M, Taylor K T, Karatza A, Vanderheyden T, Huber A, Greenwald S E, Fisk N M and Hecher K. Twin-twin transfusion syndrome: the influence of intrauterine laser photocoagulation on arterial distensibility in childhood. Circulation 2003; 107:1906-11.
10. Quintero R A, Bornick P W, Allen M H and Johson P K. Selective laser photocoagulation of communicating vessels in severe twin-twin transfusion syndrome in women with an anterior placenta. Obstet Gynecol 2001; 97:477-81.
11. Hecher K, Diehl W, Zikulnig L, Vetter M and Hackeloer B J. Endoscopic laser coagulation of placental anastomoses in 200 pregnancies with severe mid-trimester twin-to-twin transfusion syndrome. Eur J Obstet Gynecol Reprod Biol 2000; 92:135-9.
12. Ville Y, Hecher K, Gagnon A, Sebire N, Hyett J and Nicolaides K. Endoscopic laser coagulation in the management of severe twin-to-twin transfusion syndrome. Br J Obstet Gynaecol 1998; 105:446-53.
13. Deprest J A, Van Schoubroeck D, Evrard V A, Flageole H, Van Ballaer P and Vandenberghe K. Fetoscopic Nd:YAG Laser Coagulation for Twin-Twin Transfusion Syndrome in Cases of Anterior Placenta. J Am Assoc Gynecol Laparosc 1996; 3:S9.
14. Cincotta R B, Gray P H, Phythian G, Rogers Y M and Chan F Y. Long term outcome of twin-twin transfusion syndrome. Arch Dis Child Fetal Neonatal Ed 2000; 83:F171-6.
15. Fieni S, Gramellini D, Piantelli G, Verrotti C and Cavallotti D. Twin-twin transfusion syndrome: a review of treatment option. Acta Biomed Ateneo Parmense 2004; 75 Suppl 1:34-9.
16. Machin G A, Feldstein V A, van Gernert M J, Keith L G and Hecher K. Doppler sonographic demonstration of 16. arterio-venous anastomosis in monochorionic twin gestation. Ultrasound Obstet Gynecol 2000; 16:214-7.
17. Hecher K, Plath H, Bregenzer T, Hansmann M and Hackeloer B J. Endoscopic laser surgery versus serial amniocenteses in the treatment of severe twin-twin transfusion syndrome. Am J Obstet Gynecol 1999; 180:717-24.
18. Reece E A. Early and midtrimester genetic amniocenteses. Safety and outcomes. Obstet Gynecol Clin North Am 1997; 24:71-81.
19. Tabor A, Philip J, Bang J, Madsen M, Obel E B and Norgaard-Pedersen B. Needle size and risk of miscarriage after amniocentesis. Lancet 1988; 1:183-4.
20. NIHCD Consensus Conference on Antenatal Diagnosis. 1979; NIH Publication No. 80-1973.
21. Working Party of Amniocentesis: An assessment of the hazards of amniocentesis. Br J Obstet Gynecol 1978; 85:Suppl 2.
22. Yamamoto M and Ville Y. Recent findings on laser treatment of twin-to-twin transfusion syndrome. Curr Opin Obstet Gynecol 2006; 18:87-92.
23. Cavicchioni O, Yamamoto M, Robyr R, Takahashi Y and Ville Y. Intrauterine fetal demise following laser treatment in twin-to-twin transfusion syndrome. Bjog 2006; 113: 590-4.
24. Robyr R, Lewi L, Salomon L J, Yamamoto M, Bernard J P, Deprest J and Ville Y. Prevalence and management of late fetal complications following successful selective laser coagulation of chorionic plate anastomoses in twin-to-twin transfusion syndrome. Am J Obstet Gynecol 2006; 194:796-803.
25. Lewi L, Jani J, Cannie M, Robyr R, Ville Y, Hecher K, Gratacos E, Vandecruys H, Vandecaveye V, Dymarkowski S and Deprest J. Intertwin anastomoses in monochorionic placentas after fetoscopic laser coagulation for twin-to-twin transfusion syndrome: is there more than meets the eye? Am J Obstet Gynecol 2006; 194:790-5.
26. Feldstein V A. Understanding twin-twin transfusion syndrome: role of Doppler ultrasound. Ultrasound Q 2002; 18:247-54.
27. Machin G A. Twin-twin transfusion syndrome—possible roles for Doppler ultrasound and amniocentesis. Prenat Diagn 1995; 15:681-2.
28. Ohno Y, Ando H, Tanamura A, Kurauchi O, Mizutani S and Tomoda Y. The value of Doppler ultrasound in the diagnosis and management of twin-to-twin transfusion syndrome. Arch Gynecol Obstet 1994; 255:37-42.
29. Brown C, Reinhall P G, Karasawa S and Seibel E J. Optomechanical design and fabrication of resonant microscanners for a scanning fiber endoscope. Optical Engineering 2006; 45:043001.
30. Dickensheets D L and Kino G S. Micromachined scanning confocal optical microscope. Optics Letters 1996; 21:764-6.
31. Polglase A L, McLaren W J, Skinner S A, Kiesslich R, Neurath M F and Delaney P M. A fluorescence confocal endomicroscope for in vivo microscopy of the upper- and the lower-GI tract. Gastrointest Endosc 2005; 62:686-95.
32. Tearney G J, Shishkov M and Bouma B E. Spectrally encoded miniature endoscopy. Optics Letters 2002; 27:
33. Yelin D, Rizvi I, White W, Motz J, Hasan T, Bouma B E and G. J. T. Three-dimensional miniature endoscopy. Nature 2006; (in press).
34. Yelin D, Yun S H, Bouma B E and Tearney G J. Three-dimensional imaging using spectral encoding heterodyne interferometry. Opt Lett 2005; 30:1794-6.
35. Yelin D, Bouma B E, Iftimia N and Tearney G J. Three-dimensional spectrally encoded imaging. Opt Lett 2003; 28:2321-3.
36. Tearney G J, Webb R H and Bouma B E. Spectrally encoded confocal microscopy. Optics Letters 1998; 23:1152-4.
37. Yelin D, Bouma B E, Yun S H and Tearney G J. Double-clad fiber for endoscopy. Opt Lett 2004; 29:2408-10.
38. Bouma B E and Tearney G J. Power-efficient nonreciprocal interferometer and linear-scanning fiber-optic catheter for optical coherence tomography. Optics Letters 1999; 24:
39. Yun S H, Tearney G J, Vakoc B, Shishkov M, Oh W, Desjardins A, Suter M, Chan R C, Evans J A, Jang I K, Nishioka N S, de Boer J F and Bouma B E. Comprehensive volumetric microscopy in vivo. Nature Medicine 2006; (in press).
40. Jennings R. Laser surgery for vascular coagulation in twin-twin transfusion syndrome. 2006;
41. Kienle A, Lilge L I, Vitkin A, Patterson M S, Wilson B C, Hibst R and Steiner R. Why do veins appear blue? A new look at an old question. Applied Optics 1996; 35:1151-60.
42. Mendelson Y and Kent J C. Variations in optical absorption spectra of adult and fetal hemoglobins and its effect on pulse oximetry. IEEE Transactions on Biomedical Engineering 1989; 36:844-8.
43. Roggan A, Friebel M, Dorschel K, Hahn A and Muller G. Optical properties of circulating human blood in the wavelength range 400-2500 nm. Journal of Biomedical Optics 1999; 4:36-46.
44. Ishii K, Chmait R H, Martinez J M, Nakata M and Quintero R A. Ultrasound assessment of venous blood flow before and after laser therapy: approach to understanding the pathophysiology of twin-twin transfusion syndrome. Ultrasound Obstet Gynecol 2004; 24:164-8.
45. Nassif N, Cense B, Park B H, Yun S H, Chen T C, Bouma B E, Tearney G J and de Boer J F. In vivo human retinal imaging by ultrahigh-speed spectral domain optical coherence tomography. Opt Lett 2004; 29:480-2.
46. Yun S H, Tearney G J, de Boer J F and Bouma B E. High-speed spectral-domain optical coherence tomography at 1.3 µm wavelength. Optics Express 2003; 11:3598-604.
47. Schmitt J M, Xiang S H and Yung K M. Differential absorption imaging with optical coherence tomography. Journal of Optical Society A 1998; 15:2288-96.
48. Faber D J, Mik E G, Aalders M C G and van Leeuwen T G. Light absorption of (oxy-)hemoglobin assessed by spectroscopic optical coherence tomography. Optics Letters 2003; 28:1436-8.
49. Faber D J, Mik E G, Aalders M C G and van Leeuwen T G. Toward assessment of blood oxygen saturation by spectroscopic optical coherence tomography. Optics Letters 2005; 30:1015-7.
50. de Boer J F, Cense B, Park B H, Pierce M C, Tearney G J and Bouma B E Improved signal-to-noise ratio in spectral-domain compared with time-domain optical coherence tomography. Opt Left 2003; 28:2067-9.
51. Wojtkowski M, Bajraszewski T, Gorczynska I, Targowski P, Kowalczyk A, Wasilewski W and Radzewicz C. Ophthalmic imaging by spectral optical coherence tomography. Am J Ophthalmol 2004; 138:412-9.
52. Leitgeb R A, Hitzenberger C K, Fercher A F and Bajraszewski T. Phase-shifting algorithm to achieve high-speed long-depth-range probing by frequency-domain optical coherence tomography. Opt Lett 2003; 28:2201-3.
53. Leitgeb R A, Schmetterer L, Hitzenberger C K, Fercher A F, Berisha F, Wojtkowski M and Bajraszewski T. Real-time measurement of in vitro flow by Fourier-domain color Doppler optical coherence tomography. Opt Lett 2004; 29:171-3.
54. Vakoc B J, Yun S H, Tearney G J and Bouma B E. Elimination of depth degeneracy in optical frequency-domain imaging through polarization-based optical demodulation. Opt Lett 2006; 31:362-4.
55. Theoharatos C, Laskaris N A, Economou G and Fotopoulos S. A generic scheme for color image retrieval based on the multivariate Wald-Wolfowitz test. Ieee Transactions on Knowledge and Data Engineering 2005; 17:808-19.
56. Zhai H C, Liang Y M and Mu G G. Color-image retrieval based on fuzzy correlation. Science in China Series F-Information Sciences 2004; 47:295-300.
57. Bajoria R. Vascular anatomy of monochorionic placenta in relation to discordant growth and amniotic fluid volume. Hum Reprod 1998; 13:2933-40.
58. Yang V X D, Gordon M L, Qi B, Pekar J, Lo S, Seng-Yue E, Mok A, Wilson B C and Vitkin A I. High speed, wide velocity dynamic range Doppler optical coherence tomography (Part I): System design, signal processing, and performance. Optics Express 2003; 11:794-809.
59. Shah S. Damage Threshold of Replicated Gratings 1998.
60. Rowe D. High groove density grating performance at 1064 and 532 nm. 2006;

What is claimed is:

1. An apparatus for obtaining diagnostic information for a structure and modifying at least one property of at least one portion of the structure, comprising:
a source providing an electro-magnetic radiation which modifies the at least one property of the at least one portion of the structure by ablating or coagulating the at least one portion;
a fiber configured to provide therethrough the electro-magnetic radiation which includes:
a first electro-magnetic radiation having a first wavelength in a visible range,
a second electro-magnetic radiation having a second wavelength in an infrared range,
the first electro-magnetic radiation and the second electro-magnetic radiation being provided to the at least one portion of the structure,
the first electro-magnetic radiation and the second electro-magnetic radiation overlapping on the at least one portion of the structure, and
a third electro-magnetic radiation,
wherein at least one first portion of the fiber provides therethrough the first and second electro-magnetic radiations, and at least one second portion of the fiber provides the third electro-magnetic radiation to the at least one portion of the structure, and
wherein the third electro-magnetic radiation modifies the at least one property of the at least one portion of the structure;
a diffraction grating to receive the first and second electromagnetic radiations or reflections thereof from the at least one portion of the structure; and
a radiation detector electronically configured to detect a further radiation from the ablated or coagulated at least one portion of the structure provided from at least two distinct transverse locations of the at least one portion of the structure.

2. The apparatus according to claim 1, wherein the diffraction grating receives the first and second electromagnetic radiations.

3. The apparatus according to claim 1, wherein the second wavelength is a multiple of the first wavelength.

4. The apparatus according to claim 3, wherein the first wavelength is about 532 nm.

5. The apparatus of claim 1, wherein the third electro-magnetic radiation comprises a third wavelength equal to the second wavelength.

6. A method for obtaining diagnostic information for a structure and modifying at least one property of at least one portion of the structure, comprising:
providing, by a source coupled to a fiber, a first electro-magnetic radiation having a first wavelength in a visible range and a second electro-magnetic radiation having a second wavelength in an infrared range;
transmitting, by at least one first portion of the fiber, the first electro-magnetic radiation and the second electro-magnetic radiation towards the at least one portion of the structure,
the first electro-magnetic radiation and the second electro-magnetic radiation overlapping on the at least one portion of the structure;
receiving, by the at least one first portion of the fiber, reflections of the first electro-magnetic radiation and the second electro-magnetic radiation from the at least one portion of the structure;
transmitting, by at least one second portion of the fiber, a third electro-magnetic radiation to the at least one portion of the structure, the third electro-magnetic radiation modifying the at least one property of the at least one portion of the structure by ablating or coagulating the at least one portion of the structure; and
detecting, by a radiation detector optically coupled to the fiber, a further radiation from the ablated or coagulated at least one portion of the structure provided from at least two distinct transverse locations of the at least one portion to obtain the diagnostic information.

7. The method of claim 6, wherein the third electromagnetic radiation is provided by another source.

8. The method of claim 6, where the at least one first portion of the fiber is a core of the fiber and wherein the at least one second portion of the fiber is a cladding of the fiber.

9. The method of claim 6, wherein transmitting the first electro-magnetic radiation and the second electro-magnetic radiation towards the at least one portion of the structure further comprises:
transmitting the first electro-magnetic radiation and the second electro-magnetic radiation towards the at least one portion of the structure via a diffraction grating coupled to the fiber.

10. The method of claim 9, wherein transmitting the first electro-magnetic radiation and the second electro-magnetic radiation towards the at least one portion of the structure via the diffraction grating coupled to the fiber further comprises:
transmitting the first electro-magnetic radiation and the second electro-magnetic radiation towards the at least one portion of the structure through the diffraction grating coupled to the fiber.

11. The method of claim 6, wherein transmitting the first electro-magnetic radiation and the second electro-magnetic radiation towards the at least one portion of the structure further comprises:
transmitting the first electro-magnetic radiation and the second electro-magnetic radiation such that the first electro-magnetic radiation and the second electro-magnetic radiation at least partially overlap on the at least one portion of the structure.

12. The method of claim 6, wherein the third electro-magnetic radiation comprises a third wavelength equal to the second wavelength.

13. The method of claim 6, further comprising:
obtaining color information for the at least one portion of the structure based on receiving the reflections of the first electro-magnetic radiation and the second electro-magnetic radiation from the at least one portion of the structure.

* * * * *